(12) United States Patent
Lee et al.

(10) Patent No.: US 11,849,762 B2
(45) Date of Patent: Dec. 26, 2023

(54) ELECTRONIC CIGARETTE CONTROL METHOD AND DEVICE

(71) Applicant: KT&G CORPORATION, Daejeon (KR)

(72) Inventors: Jong Sub Lee, Seongnam-si (KR); Dae Nam Han, Daejeon (KR); Jung Ho Han, Daejeon (KR); Hun Ii Lim, Seoul (KR); Jang Uk Lee, Seoul (KR); Jin Young Yoon, Seoul (KR); Young Lea Kim, Seoul (KR); Ji Soo Jang, Seoul (KR); Wang Seop Lim, Anyang-s (KR); Moon Bong Lee, Seoul (KR); Soung Ho Ju, Daejeon (KR); Du Jin Park, Seoul (KR); Seong Won Yoon, Yongin-si (KR)

(73) Assignee: KT&G CORPORATION, Daejeon (KR)

( * ) Notice: Subject to any disclaimer, the term of this patent is extended or adjusted under 35 U.S.C. 154(b) by 627 days.

(21) Appl. No.: 16/635,605

(22) PCT Filed: Aug. 9, 2018

(86) PCT No.: PCT/KR2018/009094
§ 371 (c)(1),
(2) Date: Jan. 31, 2020

(87) PCT Pub. No.: WO2019/031871
PCT Pub. Date: Feb. 14, 2019

(65) Prior Publication Data
US 2020/0237014 A1    Jul. 30, 2020

(30) Foreign Application Priority Data

Aug. 9, 2017 (KR) .......................... 10-2017-0100888
Jan. 31, 2018 (KR) .......................... 10-2018-0012456

(51) Int. Cl.
*A24F 40/65* (2020.01)
*A24F 40/40* (2020.01)
(Continued)

(52) U.S. Cl.
CPC .............. *A24F 40/40* (2020.01); *A24F 40/46* (2020.01); *A24F 40/51* (2020.01); *A24F 40/57* (2020.01);
(Continued)

(58) Field of Classification Search
CPC ...................................................... A24F 40/65
See application file for complete search history.

(56) References Cited

U.S. PATENT DOCUMENTS 2,638,904 A   5/1953   Mitchell
4,585,014 A   4/1986   Fry
(Continued)

FOREIGN PATENT DOCUMENTS

CA   2 973 143 A1   8/2016
CA   2 975 654 A1   8/2016
(Continued)

OTHER PUBLICATIONS

Communication dated Jun. 29, 2020 from the Korean Intellectual Property Office in application No. 10-2018-0010836.
(Continued)

*Primary Examiner* — Cynthia Szewczyk
(74) *Attorney, Agent, or Firm* — Sughrue Mion, PLLC

(57) ABSTRACT

An electronic cigarette control device includes: a communicator configured to establish a communication connection with at least one device; and a processor configured to control an electronic cigarette according to a control message with respect to the electronic cigarette, the control
(Continued)

message being received from the at least one device through the established communication connection.

16 Claims, 16 Drawing Sheets

(51) Int. Cl.
  *A24F 40/46* (2020.01)
  *A24F 40/51* (2020.01)
  *A24F 40/60* (2020.01)
  *A24F 40/85* (2020.01)
  *A24F 40/57* (2020.01)
  *A24F 40/90* (2020.01)
  *A24F 40/20* (2020.01)

(52) U.S. Cl.
  CPC .............. *A24F 40/60* (2020.01); *A24F 40/65* (2020.01); *A24F 40/85* (2020.01); *A24F 40/20* (2020.01); *A24F 40/90* (2020.01)

(56) References Cited

U.S. PATENT DOCUMENTS

| | | |
|---|---|---|
| 4,637,407 A | 1/1987 | Bonanno et al. |
| 5,144,962 A | 9/1992 | Counts et al. |
| 5,240,012 A | 8/1993 | Ehrman et al. |
| 5,249,586 A | 10/1993 | Morgan et al. |
| 5,369,723 A | 11/1994 | Counts et al. |
| 5,388,594 A | 2/1995 | Counts et al. |
| 5,465,738 A | 11/1995 | Rowland |
| 5,479,948 A | 1/1996 | Counts et al. |
| 5,499,636 A | 3/1996 | Baggett, Jr. et al. |
| 5,591,368 A | 1/1997 | Fleischhauer et al. |
| 5,666,977 A | 9/1997 | Higgins et al. |
| 5,878,752 A | 3/1999 | Adams et al. |
| 5,967,148 A | 10/1999 | Harris et al. |
| 6,026,820 A | 2/2000 | Baggett, Jr. et al. |
| 6,040,560 A | 3/2000 | Fleischhauer et al. |
| 6,053,176 A | 4/2000 | Adams et al. |
| 6,418,938 B1 | 7/2002 | Fleischhauer et al. |
| 6,532,965 B1 | 3/2003 | Abhulimen et al. |
| 6,615,840 B1 | 9/2003 | Fournier et al. |
| 6,810,883 B2 | 11/2004 | Felter et al. |
| 7,861,726 B1 | 1/2011 | Lukasavitz |
| 8,375,959 B2 | 2/2013 | Dittrich et al. |
| 8,419,085 B2 | 4/2013 | Kim et al. |
| 8,752,545 B2 | 6/2014 | Buchberger |
| 8,851,081 B2 | 10/2014 | Fernando et al. |
| 8,973,587 B2 | 3/2015 | Liu |
| 9,078,472 B2 | 7/2015 | Liu |
| 9,078,473 B2 | 7/2015 | Worm et al. |
| 9,185,939 B2 | 11/2015 | Jarriault et al. |
| 9,220,304 B2 | 12/2015 | Greim |
| 9,271,528 B2 | 3/2016 | Liu |
| 9,320,299 B2 | 4/2016 | Hearn et al. |
| 9,423,152 B2 | 8/2016 | Ampolini et al. |
| 9,427,023 B2 | 8/2016 | Liu |
| 9,497,991 B2 | 11/2016 | Besso et al. |
| 9,499,332 B2 | 11/2016 | Fernando et al. |
| 9,504,279 B2 | 11/2016 | Chen |
| 9,516,899 B2 | 12/2016 | Plojoux et al. |
| 9,560,883 B2 | 2/2017 | Hawes |
| 9,603,388 B2 | 3/2017 | Fernando et al. |
| 9,655,383 B2 | 5/2017 | Holzherr et al. |
| 9,693,587 B2 | 7/2017 | Plojoux et al. |
| 9,723,871 B2 | 8/2017 | Xiang |
| 9,795,166 B2 | 10/2017 | Liu |
| 9,814,263 B2 | 11/2017 | Cochand et al. |
| 9,854,841 B2 | 1/2018 | Ampolini et al. |
| 9,854,845 B2 | 1/2018 | Plojoux et al. |
| 9,894,934 B2 | 2/2018 | Li et al. |
| 9,918,494 B2 | 3/2018 | Mironov et al. |
| 9,955,724 B2 | 5/2018 | Lord |
| 9,986,760 B2 | 6/2018 | Macko et al. |
| 9,999,247 B2 | 6/2018 | Ruscio et al. |
| 10,015,990 B2 | 7/2018 | Mironov |
| 10,031,183 B2 | 7/2018 | Novak, III et al. |
| 10,070,667 B2 | 9/2018 | Lord et al. |
| 10,104,911 B2 | 10/2018 | Thorens et al. |
| 10,130,780 B2 | 11/2018 | Talon |
| 10,136,673 B2 | 11/2018 | Mironov |
| 10,159,283 B2 | 12/2018 | Mironov |
| 10,194,697 B2 | 2/2019 | Fernando et al. |
| 10,299,513 B2 | 5/2019 | Perez et al. |
| 10,368,584 B2 | 8/2019 | Fernando et al. |
| 10,439,419 B2 | 10/2019 | Bernauer et al. |
| 10,440,987 B2 | 10/2019 | Zeng et al. |
| 10,448,670 B2 | 10/2019 | Talon et al. |
| 10,492,542 B1 | 12/2019 | Worm et al. |
| 10,548,350 B2 | 2/2020 | Griem et al. |
| 10,555,553 B2 | 2/2020 | Binassi et al. |
| 10,555,555 B2 | 2/2020 | Fernando et al. |
| 10,588,351 B2 | 3/2020 | Ricketts |
| 10,617,149 B2 | 4/2020 | Malgat et al. |
| 10,645,971 B2 | 5/2020 | Zitzke |
| 10,667,329 B2 | 5/2020 | Bernauer et al. |
| 10,668,058 B2 | 6/2020 | Rose et al. |
| 10,716,329 B2 | 7/2020 | Matsumoto et al. |
| 10,757,975 B2 | 9/2020 | Batista et al. |
| 10,813,174 B2 | 10/2020 | Schneider et al. |
| 10,869,503 B2 | 12/2020 | Yamada et al. |
| 10,881,131 B2 | 1/2021 | Matsumoto et al. |
| 10,881,137 B2 | 1/2021 | Suzuki et al. |
| 10,881,143 B2 | 1/2021 | Suzuki et al. |
| 11,039,642 B2 | 6/2021 | Zuber et al. |
| 11,147,316 B2 | 10/2021 | Farine et al. |
| 11,445,576 B2 | 9/2022 | Zinovik et al. |
| 2004/0261802 A1 | 12/2004 | Griffin et al. |
| 2005/0045198 A1 | 3/2005 | Larson et al. |
| 2005/0172976 A1 | 8/2005 | Newman et al. |
| 2006/0030214 A1 | 2/2006 | Katou et al. |
| 2008/0001052 A1 | 1/2008 | Kalous et al. |
| 2009/0283103 A1 | 11/2009 | Nielsen et al. |
| 2010/0001538 A1 | 1/2010 | Kim et al. |
| 2010/0024834 A1 | 2/2010 | Oglesby et al. |
| 2010/0307518 A1 | 12/2010 | Wang |
| 2011/0155151 A1 | 6/2011 | Newman et al. |
| 2011/0209717 A1 | 9/2011 | Han |
| 2011/0226236 A1 | 9/2011 | Buchberger |
| 2011/0265806 A1 | 11/2011 | Alarcon et al. |
| 2011/0290248 A1 | 12/2011 | Schennum |
| 2011/0290269 A1 | 12/2011 | Shimizu |
| 2012/0048266 A1 | 3/2012 | Alelov |
| 2012/0247494 A1 | 10/2012 | Oglesby et al. |
| 2013/0014772 A1 | 1/2013 | Liu |
| 2013/0037041 A1 | 2/2013 | Worm et al. |
| 2013/0074657 A1 | 3/2013 | Buchberger |
| 2013/0213419 A1 | 8/2013 | Tucker et al. |
| 2013/0284192 A1 | 10/2013 | Peleg et al. |
| 2013/0319439 A1 | 12/2013 | Gorelick et al. |
| 2013/0319999 A1 | 12/2013 | Plojoux et al. |
| 2013/0340775 A1 | 12/2013 | Juster et al. |
| 2014/0014125 A1 | 1/2014 | Fernando et al. |
| 2014/0020698 A1 | 1/2014 | Fiebelkorn |
| 2014/0096782 A1 | 4/2014 | Ampolini et al. |
| 2014/0116455 A1 | 5/2014 | Youn |
| 2014/0246035 A1 | 9/2014 | Minskoff et al. |
| 2014/0299137 A1 | 10/2014 | Kieckbusch et al. |
| 2014/0301721 A1 | 10/2014 | Ruscio et al. |
| 2014/0305448 A1 | 10/2014 | Zuber et al. |
| 2014/0318559 A1 | 10/2014 | Thorens et al. |
| 2014/0345634 A1 | 11/2014 | Zuber et al. |
| 2014/0363145 A1 | 12/2014 | Plojoux et al. |
| 2015/0007838 A1 | 1/2015 | Fernando et al. |
| 2015/0013696 A1 | 1/2015 | Plojoux et al. |
| 2015/0020832 A1 | 1/2015 | Greim et al. |
| 2015/0024355 A1 | 1/2015 | Ghofrani et al. |
| 2015/0027474 A1 | 1/2015 | Zuber et al. |
| 2015/0100441 A1 | 4/2015 | Alarcon et al. |
| 2015/0136124 A1 | 5/2015 | Aronie et al. |
| 2015/0136154 A1 | 5/2015 | Mitrev et al. |
| 2015/0181942 A1 | 7/2015 | Holzherr et al. |
| 2015/0208725 A1 | 7/2015 | Tsai |

(56) References Cited

U.S. PATENT DOCUMENTS

| | | |
|---|---|---|
| 2015/0208730 A1 | 7/2015 | Li et al. |
| 2015/0245654 A1 | 9/2015 | Memari et al. |
| 2015/0245666 A1 | 9/2015 | Memari et al. |
| 2015/0257445 A1 | 9/2015 | Henry, Jr. et al. |
| 2015/0272211 A1 | 10/2015 | Chung |
| 2016/0150824 A1 | 6/2016 | Memari et al. |
| 2016/0235121 A1 | 8/2016 | Rogan et al. |
| 2016/0270437 A1 | 9/2016 | Nappi |
| 2016/0286861 A1 | 10/2016 | Liu |
| 2016/0302488 A1 | 10/2016 | Fernando et al. |
| 2016/0331032 A1 | 11/2016 | Malgat et al. |
| 2016/0345629 A1 | 12/2016 | Mironov |
| 2016/0366933 A1 | 12/2016 | Liu |
| 2016/0366946 A1 | 12/2016 | Murison et al. |
| 2016/0374402 A1 | 12/2016 | Fernando et al. |
| 2017/0006916 A1 | 1/2017 | Liu |
| 2017/0006919 A1 | 1/2017 | Liu |
| 2017/0027229 A1 | 2/2017 | Cameron |
| 2017/0027234 A1 | 2/2017 | Farine et al. |
| 2017/0042243 A1 | 2/2017 | Plojoux et al. |
| 2017/0055580 A1 | 3/2017 | Blandino et al. |
| 2017/0065002 A1 | 3/2017 | Fernando et al. |
| 2017/0071251 A1 | 3/2017 | Goch |
| 2017/0071259 A1 | 3/2017 | Yamada et al. |
| 2017/0095006 A1 | 4/2017 | Egoyants et al. |
| 2017/0150757 A1 | 6/2017 | Worm et al. |
| 2017/0164659 A1 | 6/2017 | Schneider et al. |
| 2017/0172214 A1 | 6/2017 | Li et al. |
| 2017/0172215 A1 | 6/2017 | Li et al. |
| 2017/0188634 A1 | 7/2017 | Plojoux et al. |
| 2017/0295844 A1 | 10/2017 | Thevenaz et al. |
| 2018/0043114 A1* | 2/2018 | Bowen .................. A24F 40/65 |
| 2018/0177234 A1 | 6/2018 | Lee |
| 2018/0206556 A1 | 7/2018 | Thorens et al. |
| 2018/0235283 A1 | 8/2018 | Zuber et al. |
| 2019/0014826 A1 | 1/2019 | Thorens et al. |
| 2019/0075849 A1 | 3/2019 | Hawes |
| 2019/0320719 A1 | 10/2019 | Liu et al. |
| 2019/0364975 A1 | 12/2019 | Fernando et al. |
| 2020/0006950 A1 | 1/2020 | Holzherr |
| 2020/0120983 A1 | 4/2020 | Chen |
| 2020/0232766 A1 | 7/2020 | Flick |
| 2020/0305508 A1 | 10/2020 | Talon |
| 2020/0352224 A1 | 11/2020 | Plojoux et al. |
| 2020/0413495 A1 | 12/2020 | Schneider et al. |
| 2021/0000182 A1 | 1/2021 | Ruscio et al. |
| 2021/0120875 A1 | 4/2021 | Mironov |

FOREIGN PATENT DOCUMENTS

| | | | |
|---|---|---|---|
| CH | 310239 | A | 12/1955 |
| CN | 2146758 | Y | 11/1993 |
| CN | 1102964 | A | 5/1995 |
| CN | 1122213 | A | 5/1996 |
| CN | 1190335 | A | 8/1998 |
| CN | 1209731 | A | 3/1999 |
| CN | 2857109 | Y | 1/2007 |
| CN | 1973706 | A | 6/2007 |
| CN | 101043827 | A | 9/2007 |
| CN | 101444335 | A | 6/2009 |
| CN | 201491717 | U | 6/2010 |
| CN | 101940369 | A | 1/2011 |
| CN | 102006790 | A | 4/2011 |
| CN | 102109393 | A | 6/2011 |
| CN | 102326869 | A | 1/2012 |
| CN | 102438470 | A | 5/2012 |
| CN | 202407082 | U | 9/2012 |
| CN | 202774134 | U | 3/2013 |
| CN | 103096741 | A | 5/2013 |
| CN | 103281920 | A | 9/2013 |
| CN | 103338665 | A | 10/2013 |
| CN | 103622162 | A | 3/2014 |
| CN | 203457802 | U | 3/2014 |
| CN | 203575658 | U | 5/2014 |
| CN | 103859606 | A | 6/2014 |
| CN | 203633505 | U | 6/2014 |
| CN | 203646503 | U | 6/2014 |
| CN | 103929988 | A | 7/2014 |
| CN | 203689071 | U | 7/2014 |
| CN | 203692545 | U | 7/2014 |
| CN | 103974638 | A | 8/2014 |
| CN | 103974640 | A | 8/2014 |
| CN | 103987286 | A | 8/2014 |
| CN | 103997921 | A | 8/2014 |
| CN | 103997922 | A | 8/2014 |
| CN | 203789137 | U | 8/2014 |
| CN | 104023568 | A | 9/2014 |
| CN | 104023574 | A | 9/2014 |
| CN | 104039183 | A | 9/2014 |
| CN | 203814592 | U | 9/2014 |
| CN | 104095295 | A | 10/2014 |
| CN | 104106842 | A | 10/2014 |
| CN | 203943078 | U | 11/2014 |
| CN | 204070570 | U | 1/2015 |
| CN | 204146338 | U | 2/2015 |
| CN | 102811634 | B | 3/2015 |
| CN | 104382237 | A | 3/2015 |
| CN | 104470387 | A | 3/2015 |
| CN | 104489933 | A | 4/2015 |
| CN | 104544559 | A | 4/2015 |
| CN | 204317504 | U | 5/2015 |
| CN | 104754964 | A | 7/2015 |
| CN | 104770878 | A | 7/2015 |
| CN | 104799438 | A | 7/2015 |
| CN | 104812260 | A | 7/2015 |
| CN | 204444239 | U | 7/2015 |
| CN | 204763414 | U | 11/2015 |
| CN | 105163610 | A | 12/2015 |
| CN | 105208882 | A | 12/2015 |
| CN | 105208884 | A | 12/2015 |
| CN | 105341993 | A | 2/2016 |
| CN | 105342011 | A | 2/2016 |
| CN | 105357994 | A | 2/2016 |
| CN | 205018293 | U | 2/2016 |
| CN | 105361250 | A | 3/2016 |
| CN | 105453598 | A | 3/2016 |
| CN | 205072064 | U | 3/2016 |
| CN | 205180371 | U | 4/2016 |
| CN | 205197003 | U | 5/2016 |
| CN | 205337598 | U | 6/2016 |
| CN | 105747281 | A | 7/2016 |
| CN | 105789506 | A | 7/2016 |
| CN | 105831812 | A | 8/2016 |
| CN | 105848503 | A | 8/2016 |
| CN | 105876869 | A | 8/2016 |
| CN | 205456048 | U | 8/2016 |
| CN | 205512358 | U | 8/2016 |
| CN | 105939625 | A | 9/2016 |
| CN | 205597118 | U | 9/2016 |
| CN | 106037014 | A | 10/2016 |
| CN | 205648910 | U | 10/2016 |
| CN | 106102492 | A | 11/2016 |
| CN | 106132217 | A | 11/2016 |
| CN | 106163307 | A | 11/2016 |
| CN | 205728067 | U | 11/2016 |
| CN | 106174699 | A | 12/2016 |
| CN | 106231934 | A | 12/2016 |
| CN | 205831062 | U | 12/2016 |
| CN | 106413439 | A | 2/2017 |
| CN | 106413444 | A | 2/2017 |
| CN | 106455708 | A | 2/2017 |
| CN | 106455714 | A | 2/2017 |
| CN | 106455716 | A | 2/2017 |
| CN | 106473233 | A | 3/2017 |
| CN | 106535680 | A | 3/2017 |
| CN | 206097720 | U | 4/2017 |
| CN | 206197012 | U | 5/2017 |
| CN | 106901404 | A | 6/2017 |
| CN | 206312988 | U | 7/2017 |
| DE | 3302518 | A1 | 7/1984 |
| DE | 20 2014 004 361 | U1 | 10/2015 |
| EA | 012169 | B1 | 8/2009 |
| EA | 026076 | B1 | 2/2017 |
| EP | 1119267 | B1 | 7/2004 |

(56) References Cited

FOREIGN PATENT DOCUMENTS

| | | |
|---|---|---|
| EP | 2 110 033 A1 | 10/2009 |
| EP | 2 201 850 A1 | 6/2010 |
| EP | 2253233 A1 | 11/2010 |
| EP | 2 022 349 B1 | 7/2014 |
| EP | 2 531 053 B1 | 9/2015 |
| EP | 3 098 738 A1 | 11/2016 |
| EP | 2 432 339 B1 | 3/2017 |
| EP | 3 179 828 A1 | 6/2017 |
| EP | 3 248 485 B1 | 4/2020 |
| EP | 3 275 319 B1 | 8/2020 |
| GB | 2542018 A | 3/2017 |
| GB | 2550540 A | 11/2017 |
| JP | 3-232481 A | 10/1991 |
| JP | 7-184627 A | 7/1995 |
| JP | 11-40122 A | 2/1999 |
| JP | 11-164679 A | 6/1999 |
| JP | 3645921 B2 | 5/2005 |
| JP | 2006-92831 A | 4/2006 |
| JP | 2006-320286 A | 11/2006 |
| JP | 4278306 B2 | 6/2009 |
| JP | 2010-526553 A | 8/2010 |
| JP | 2011-87569 A | 5/2011 |
| JP | 2011-518567 A | 6/2011 |
| JP | 4739433 B2 | 8/2011 |
| JP | 2012-527222 A | 11/2012 |
| JP | 2014-500017 A | 1/2014 |
| JP | 2014-79229 A | 5/2014 |
| JP | 2014-521419 A | 8/2014 |
| JP | 2014-525237 A | 9/2014 |
| JP | 2014-533513 A | 12/2014 |
| JP | 2014-534813 A | 12/2014 |
| JP | 2015-503916 A | 2/2015 |
| JP | 2015-504669 A | 2/2015 |
| JP | 2015-506170 A | 3/2015 |
| JP | 2015-507477 A | 3/2015 |
| JP | 2015-508996 A | 3/2015 |
| JP | 2015-524261 A | 8/2015 |
| JP | 2015-180214 A | 10/2015 |
| JP | 2015-529458 A | 10/2015 |
| JP | 2015-204833 A | 11/2015 |
| JP | 2016-528910 A | 9/2016 |
| JP | 2016-538848 A | 12/2016 |
| JP | 2017-501682 A | 1/2017 |
| JP | 2017-46700 A | 3/2017 |
| JP | 2017-51189 A | 3/2017 |
| JP | 2017-70297 A | 4/2017 |
| JP | 2017-514463 A | 6/2017 |
| KR | 10-0304044 B1 | 11/2001 |
| KR | 10-0806461 B1 | 2/2008 |
| KR | 20-2009-0008911 U | 9/2009 |
| KR | 10-0965099 B1 | 6/2010 |
| KR | 10-1001077 B1 | 12/2010 |
| KR | 10-2011-0096548 A | 8/2011 |
| KR | 20-2011-0009632 U | 10/2011 |
| KR | 10-1098112 B1 | 12/2011 |
| KR | 10-2012-0027029 A | 3/2012 |
| KR | 10-2012-0101637 A | 9/2012 |
| KR | 10-1184499 B1 | 9/2012 |
| KR | 10-2012-0109634 A | 10/2012 |
| KR | 10-2012-0114333 A | 10/2012 |
| KR | 10-2012-0121314 A | 11/2012 |
| KR | 10-2013-0027909 A | 3/2013 |
| KR | 20-0466757 Y1 | 5/2013 |
| KR | 10-2013-0081238 A | 7/2013 |
| KR | 20-0469513 Y1 | 10/2013 |
| KR | 10-2013-0139296 A | 12/2013 |
| KR | 10-2014-0068203 A | 6/2014 |
| KR | 10-2014-0092312 A | 7/2014 |
| KR | 10-2014-0109455 A | 9/2014 |
| KR | 10-2014-0114554 A | 9/2014 |
| KR | 10-2014-0116055 A | 10/2014 |
| KR | 10-2014-0118983 A | 10/2014 |
| KR | 10-2014-0119072 A | 10/2014 |
| KR | 10-2014-0135774 A | 11/2014 |
| KR | 20-2014-0006242 U | 12/2014 |
| KR | 10-2015-0030409 A | 3/2015 |
| KR | 10-2015-0033617 A | 4/2015 |
| KR | 10-2015-0058569 A | 5/2015 |
| KR | 10-1516304 B1 | 5/2015 |
| KR | 10-1523088 B1 | 5/2015 |
| KR | 10-1523088 B2 | 5/2015 |
| KR | 10-2015-0099771 A | 9/2015 |
| KR | 10-2016-0009678 A | 1/2016 |
| KR | 10-2016-0012110 A | 2/2016 |
| KR | 10-2016-0012329 A | 2/2016 |
| KR | 10-2016-0015144 A | 2/2016 |
| KR | 10-2016-0040643 A | 4/2016 |
| KR | 10-1609715 B1 | 4/2016 |
| KR | 10-1614171 B1 | 4/2016 |
| KR | 10-2015-0058569 A | 5/2016 |
| KR | 10-2016-0052607 A | 5/2016 |
| KR | 10-1619032 B1 | 5/2016 |
| KR | 20-2016-0001476 U | 5/2016 |
| KR | 10-2016-0060006 A | 6/2016 |
| KR | 10-2016-0088163 A | 7/2016 |
| KR | 10-2016-0094938 A | 8/2016 |
| KR | 10-2016-0096744 A | 8/2016 |
| KR | 10-2016-0108855 A | 9/2016 |
| KR | 10-1656061 B1 | 9/2016 |
| KR | 10-2016-0114743 A | 10/2016 |
| KR | 10-2016-0124091 A | 10/2016 |
| KR | 10-1667124 B1 | 10/2016 |
| KR | 10-1668175 B1 | 10/2016 |
| KR | 10-2016-0129024 A | 11/2016 |
| KR | 10-2016-0131035 A | 11/2016 |
| KR | 10-2016-0133665 A | 11/2016 |
| KR | 10-2016-0137627 A | 11/2016 |
| KR | 10-1679489 B1 | 11/2016 |
| KR | 10-2016-0140608 A | 12/2016 |
| KR | 10-2016-0142896 A | 12/2016 |
| KR | 10-2016-0147253 A | 12/2016 |
| KR | 10-1690389 B1 | 12/2016 |
| KR | 10-2017-0006282 A | 1/2017 |
| KR | 10-2017-0007262 A | 1/2017 |
| KR | 10-2017-0044158 A | 4/2017 |
| KR | 10-2017-0071486 A | 6/2017 |
| KR | 10-2017-0074898 A | 6/2017 |
| KR | 10-1740160 B1 | 6/2017 |
| RU | 2302806 C2 | 7/2007 |
| RU | 2425608 C2 | 8/2011 |
| RU | 2531890 C2 | 10/2014 |
| RU | 2564600 C1 | 10/2015 |
| RU | 2014 125 232 A | 12/2015 |
| RU | 2014125232 A | 12/2015 |
| RU | 2581999 C2 | 4/2016 |
| RU | 2589437 C2 | 7/2016 |
| RU | 2594557 C2 | 8/2016 |
| RU | 2595593 C2 | 8/2016 |
| RU | 2 602 962 C2 | 11/2016 |
| RU | 2 603 559 C2 | 11/2016 |
| RU | 2602053 C2 | 11/2016 |
| RU | 2602962 C2 | 11/2016 |
| RU | 2604012 C2 | 12/2016 |
| UA | 104628 C2 | 2/2014 |
| UA | 112169 C2 | 8/2016 |
| WO | 94/06314 A1 | 3/1994 |
| WO | 98/23171 A1 | 6/1998 |
| WO | 00/27232 A1 | 5/2000 |
| WO | 2009/118085 A1 | 10/2009 |
| WO | 2010/133342 A1 | 11/2010 |
| WO | 2011/028372 A1 | 3/2011 |
| WO | 2011/095781 A1 | 8/2011 |
| WO | 2012/072264 A1 | 6/2012 |
| WO | 2012/123702 A1 | 9/2012 |
| WO | 2013/034458 A1 | 3/2013 |
| WO | 2013/060743 A2 | 5/2013 |
| WO | 2013/076098 A2 | 5/2013 |
| WO | 2013/093695 A1 | 6/2013 |
| WO | 2013/098395 A1 | 7/2013 |
| WO | 2013/098398 A3 | 7/2013 |
| WO | 2013/102609 A2 | 7/2013 |
| WO | 2013/102612 A2 | 7/2013 |
| WO | 2013/120565 A3 | 8/2013 |
| WO | 2013/126777 A2 | 8/2013 |

(56) References Cited

FOREIGN PATENT DOCUMENTS

| | | | |
|---|---|---|---|
| WO | 2013/137084 A1 | 9/2013 |
| WO | 2013/171217 A1 | 11/2013 |
| WO | 2014/029880 A2 | 2/2014 |
| WO | 2014/102092 A1 | 7/2014 |
| WO | 2015/046386 A1 | 4/2015 |
| WO | 2015/088744 A1 | 6/2015 |
| WO | 2015088744 A1 | 6/2015 |
| WO | 2015/128665 A1 | 9/2015 |
| WO | 2015128665 A1 | 9/2015 |
| WO | 2015/155289 A1 | 10/2015 |
| WO | 2015/165813 A1 | 11/2015 |
| WO | 2015/174657 A1 | 11/2015 |
| WO | 2015/177044 A1 | 11/2015 |
| WO | 2015/197627 A1 | 12/2015 |
| WO | 2016/012811 A1 | 1/2016 |
| WO | 2016/187803 A | 1/2016 |
| WO | 2016/059073 A1 | 4/2016 |
| WO | 2016/075028 A1 | 5/2016 |
| WO | 2016/076147 A1 | 5/2016 |
| WO | 2016075028 A1 | 5/2016 |
| WO | 2016/107766 A1 | 7/2016 |
| WO | 2016/124550 A1 | 8/2016 |
| WO | 2016/124552 A1 | 8/2016 |
| WO | 2016/150019 A1 | 9/2016 |
| WO | 2016/156103 A1 | 10/2016 |
| WO | 2016/156219 A1 | 10/2016 |
| WO | 2016/159013 A1 | 10/2016 |
| WO | 2016166064 A1 | 10/2016 |
| WO | 2016178377 A1 | 11/2016 |
| WO | 2017/029088 A1 | 2/2017 |
| WO | 2017/029089 A1 | 2/2017 |
| WO | 2017/037457 A1 | 3/2017 |
| WO | 2017/042297 A1 | 3/2017 |
| WO | 2017/075759 A1 | 5/2017 |
| WO | 2017/139963 A1 | 8/2017 |
| WO | 2018/050449 A1 | 3/2018 |
| WO | 2018/189195 A1 | 10/2018 |
| WO | 2019/020826 A1 | 1/2019 |
| WO | 2019/030172 A1 | 2/2019 |
| WO | 2019/095268 A1 | 5/2019 |

OTHER PUBLICATIONS

Communication dated Oct. 29, 2020 from the Korean Intellectual Property Office in application No. 10-2018-0010837.
Decision on Grant of a Patent For Invention dated Nov. 26, 2020 from Russian Federal Service for Intellectual Property in Application No. 2020124607/03.
Decision on Grant of a Patent For Invention dated Oct. 26, 2020 from Russian Federal Service for Intellectual Property in Application No. 2020124610/03.
Extended European Search Report dated Nov. Aug. 3, 2020 from the European Patent Office in EP Application No. 17880867.1.
Office Action dated Nov. 26, 2020 from the Russian Federal Service for Intellectual Property in Application No. 2020124609/03.
Office Action dated Nov. 4, 2020 from the Japanese Patent Office in Application No. 2019-554453.
Office Action dated Nov. 4, 2020 from the Japanese Patent Office in Application No. 2020-128346.
Partial Supplementary European Search Report dated Aug. 3, 2020 from the European Patent Office in EP Application No. 17880867.1.
Office Action dated Apr. 2, 2019 in Korean Application No. 10-2019-0021286, English Translation.
Office Action dated Apr. 25, 2019 in Korean Application No. 10-2019-0033721, English Translation.
Office Action dated Apr. 25, 2019 in Korean Application No. 10-2019-0033784, English Translation.
Office Action dated Apr. 3, 2019 in Korean Application No. 10-2019-0018812, English Translation.
Office Action dated Apr. 4, 2019 in Korean Application No. 10-2019-0019194, English Translation.
Office Action dated Apr. 4, 2019 in Korean Application No. 10-2019-0019195, English Translation.
Office Action dated Apr. 4, 2019 in Korean Application No. 10-2019-0020484, English Translation.
Office Action dated Apr. 9, 2021 in Korean Application No. 10-2020-0116256, English Translation.
Extended European Search Report dated Apr. 1, 2021 in European Application No. 18805933.1.
Extended European Search Report dated Jan. 15, 2021 in European Application No. 20188949.0.
Extended European Search Report dated Jul. 1, 2021 in European Application No. 18854661.8.
Extended European Search Report dated Jun. 14, 2021 in European Application No. 18842951.8.
Extended European Search Report dated Jun. 16, 2021 in European Application No. 18853434.1.
Office Action dated Jul. 22, 2021 in Korean Application No. 10-2021-0051359, English Translation.
Office Action dated Jun. 29, 2021 in Chinese Application No. 201880022072.2, English Translation.
Office Action dated May 5, 2021 in Canadian Application No. 3,047,236.
International Search Report dated Jul. 24, 2018 in International Application No. PCT/KR2018/003691, English Translation.
International Search Report dated Nov. 14, 2018 in International Application No. PCT/KR2018/004118.
International Search Report dated Nov. 6, 2018 in International Application No. PCT/KR2018/004129.
International Search Report dated Nov. 6, 2018 in International Application No. PCT/KR2018/004130.
International Search Report dated Nov. 6, 2018 in International Application No. PCT/KR2018/004178.
International Search Report dated Sep. 6, 2018 in International Application No. PCT/KR2018/004176.
International Search Report dated Sep. 7, 2018 in International Application No. PCT/KR2018/004171.
International Search Report dated Sep. 7, 2018 in International Application No. PCT/KR2018/004172.
Office Action dated Apr. 5, 2019 in Korean Application No. 10-2019-0027638, English Translation.
Office Action dated May 27, 2020 in Russian Application No. 2019121813, English Translation.
Office Action dated Aug. 16, 2021 in Chinese Application No. 201880024006.9, English Translation.
Office Action dated Aug. 26, 2021 in Chinese Application No. 201880024107.6, English Translation.
Office Action dated Aug. 4, 2021 in Chinese Application No. 201880024289.7, English Translation.
Office Action dated Jul. 26, 2021 in Chinese Application No. 201880024059.0, English Translation.
Office Action dated Jul. 16, 2021 in Chinese Application No. 201880024367.3, English Translation.
Office Action dated Jul. 19, 2021 in Chinese Application No. 201880024070.7, English Translation.
International Search Report dated Aug. 29, 2018 in International Application No. PCT/KR2018/005945, English Translation.
International Search Report dated Nov. 30, 2018 in International Application No. PCT/KR2018/006702, English Translation.
International Search Report dated Dec. 4, 2018 in International Application No. PCT/KR2018/006747, English Translation.
Office Action dated Jul. 27, 2021 in Chinese Application No. 201780084891.5, English Translation.
Communication dated Mar. 14, 2022 from the Chinese Patent Office in Chinese Application No. 201880024059.0.
Communication dated Feb. 28, 2022 from the Chinese Patent Office in Chinese Application No. 201880050526.7.
Office Action dated Sep. 24, 2020 in Korean Application No. 10-2018-0012456, English Translation.
Extended European Search Report dated Dec. 11, 2020 in European Application No. 20188967.2.
Extended European Search Report dated Dec. 16, 2020 in European Application No. 20188985.4.

(56) References Cited

OTHER PUBLICATIONS

Office Action dated Dec. 30, 2020 in Russian Application No. 2020124651, English Translation.
Office Action dated Dec. 28, 2020 in Russian Application No. 2020124652, English Translation.
Office Action dated Dec. 11, 2020 in Russian Application No. 2020124653, English Translation.
Office Action dated Jan. 22, 2021 in Russian Application No. 2020124657, English Translation.
Office Action dated Jan. 22, 2021 in Russian Application No. 2020124658, English Translation.
Extended European Search Report dated Dec. 18, 2020 in European Application No. 18775504.6.
Office Action dated Jan. 19, 2021 in Japanese Application No. 2019-553569, English Translation.
Extended European Search Report dated Jan. 14, 2021 in European Application No. 18784738.9.
Extended European Search Report dated Dec. 10, 2020 in European Application No. 20188932.6.
Office Action dated Jan. 12, 2021 in Japanese Application No. 2019-555201, English Translation.
Office Action dated Jan. 12, 2021 in Japanese Application No. 2019-555169, English Translation.
Office Action dated Jan. 5, 2021 in Japanese Application No. 2019-558557, English Translation.
Extended European Search Report dated Nov. 19, 2020 in European Application No. 20188792.4.
Office Action dated Dec. 1, 2020 in Japanese Application No. 2020-501188, English Translation.
Extended European Search Report dated Dec. 18, 2020 in European Application No. 20188926.8.
Office Action dated Jan. 19, 2021 in Japanese Application No. 2020-501514, English Translation.
Office Action dated May 28, 2020 in Korean Application No. 10-2017-0147605, English Translation.
Office Action dated Sep. 29, 2021 in Chinese Application No. 201880024311.8, English Translation.
Office Action dated Sep. 24, 2021 in Chinese Application No. 201880024010.5, English Translation.
Office Action dated Sep. 29, 2021 in Chinese Application No. 201880024276.X, English Translation.
Office Action dated Oct. 28, 2021 in Chinese Application No. 201880046418.2, English Translation.
Extended European Search Report dated Oct. 27, 2021 in European Application No. 18844735.3.
Office Action dated Sep. 17, 2021 in Chinese Application No. 201880030699.2, English Translation.
Extended European Search Report dated Jan. 14, 2021 in European Application No. 18783776.0.
Extended European Search Report dated Jan. 25, 2021 in European Application No. 18785166.2.
Extended European Search Report dated Jan. 29, 2021 in European Application No. 18784464.2.
Extended European Search Report dated Mar. 15, 2021 in European Application No. 18785061.5.
Extended European Search Report dated Mar. 19, 2021 in European Application No. 18784164.8.
Extended European Search Report dated Mar. 24, 2021 in European Application No. 18784268.7.
Extended European Search Report dated Mar. 25, 2021 in European Application No. 18784370.1.
Extended European Search Report dated Mar. 25, 2021 in European Application No. 18784841.1.
Office Action dated Feb. 24, 2021 in Japanese Application No. 2019-555168, English Translation.
Office Action dated Feb. 24, 2021 in Japanese Application No. 2019-555203, English Translation.
Office Action dated Feb. 24, 2021 in Japanese Application No. 2019-555204, English Translation.
Office Action dated Feb. 4, 2021 in Russian Application No. 2020124609, English Translation.
Office Action dated Feb. 9, 2021 in Japanese Application No. 2019-555184, English Translation.
Office Action dated Jan. 26, 2021 in Japanese Application No. 2020-501521, English Translation.
Office Action dated Mar. 2, 2021 in Japanese Application No. 2019-555170, English Translation.
Office Action dated Mar. 2, 2021 in Japanese Application No. 2019-555182, English Translation.
Office Action dated Mar. 30, 2021 in Japanese Application No. 2020-501377, English Translation.
Office Action dated Jan. 19, 2021 in Indonesian Application No. P00201906007, English Translation.
Communication dated Feb. 13, 2020, from the Korean Intellectual Property Office in application No. 10-2018-0010837.
Communication dated Dec. 1, 2021 from the Chinese Patent Office in Chinese Application No. 201880046367.3.
Communication dated Nov. 25, 2021 from the Chinese Patent Office in Chinese Application No. 201880047174.X.
Communication dated Jan. 8, 2020, issued by the Korean Intellectual Property Office in Korean Application No. 10-2017-0119664.
Communication dated Jan. 3, 2020, issued by the Korean Intellectual Property Office in Korean Application No. 10-2018-0018693.
Communication dated Jan. 3, 2020, issued by the Korean Intellectual Property Office in Korean Application No. 10-2018-0012456.
Communication dated Feb. 13, 2020, issued by the Korean Intellectual Property Office in Korean Application No. 10-2018-0010837.
Communication dated Feb. 7, 2020, issued by the Korean Intellectual Property Office in Korean Application No. 10-2017-0146697.
Communication dated Jul. 3, 2019, issued by the Korean Intellectual Property Office in Korean Application No. 10-2019-0017391.
Communication dated Dec. 11, 2019, issued by the Korean Intellectual Property Office in Korean Application No. 10-2018-0010841.
International Search Report in International Application No. PCT/KR2018/009100, dated Feb. 28, 2019.
International Search Report in International Application No. PCT/KR2018/009094, dated Nov. 26, 2018.
International Search Report in International Application No. PCT/KR2018/004179, dated Sep. 6, 2018.
International Search Report in International Application No. PCT/KR2017/012486, dated May 29, 2018.
Office Action dated Nov. 22, 2022 in Chinese Application No. 202010762996.5, English Translation.
Office Action dated Oct. 24, 2022 in Ukrainian Application No. a 2020 04868, English Translation.
Office Action dated Oct. 27, 2022 in Ukrainian Application No. a 2020 04869, English Translation.
Office Action dated Dec. 30, 2022 in Chinese Application No. 202010756239.7, English Translation.
Office Action dated Dec. 13, 2022 in Japanese Application No. 2021-165298, English Translation.
Office Action dated Nov. 2, 2022 in Chinese Application No. 201880050526.7, English Translation.
Office Action dated Sep. 20, 2022 issued by the Japanese Patent Office in Japanese Application No. 2021-174035, Machine Translation.
Office Action dated Aug. 12, 2022 issued by the Chinese Patent Office in Chinese Application No. 201880024059.0, Machine Translation.
Office Action dated May 30, 2022 issued by the Canadian Patent Office in Canadian Application No. 3,080,145.
Office Action dated May 29, 2022 issued by the Intellectual Property Office of the Philippines in Philippine Application No. 1/2019/501361.
Office Action dated Jun. 28, 2022 issued by the Japanese Patent Office in Japanese Application No. 2021-075028, Machine Translation.
Notice of Reasons of Refusal dated Jan. 10, 2023 from the Japanese Patent Office in Application No. 2021-177649, English Translation.

(56) References Cited

OTHER PUBLICATIONS

Chinese Office Action dated Jan. 28, 2023 in Chinese Application No. 202010763214.X, English Translation.
Chinese Office Action dated Jan. 3, 2023 in Chinese Application No. 202010760979.8, English Translation.
Chinese Office Action dated Jan. 10, 2023 in Chinese Application No. 202010780990.4, English Translation.
Office Action dated Jun. 1, 2023 in Korean Application No. 10-2022-0148790.
Office Action dated Jul. 12, 2023 in Ukrainian Application No. a 2021 04884.
Office Action dated May 9, 2023 in Japanese Application No. 2022-086448.
Communication dated Jul. 10, 2023 in European Application No. 18 785 166.2.
Chinese Office Action dated Jul. 31, 2023 in Application No. 201880050526.7.
Communication issued in the European Patent Office dated Nov. 3, 2023 in corresponding European Patent Application No. 18 775 504.6-1105.

\* cited by examiner

ELECTRONIC CIGARETTE CONTROL METHOD AND DEVICE

CROSS REFERENCE TO RELATED APPLICATIONS

This application is a National Stage of International Application No. PCT/KR2018/009094 filed Aug. 9, 2018, claiming priority based on Korean Patent Application No. 10-2017-0100888 filed Aug. 9, 2017 and Korean Patent Application No. 10-2018-0012456 filed Jan. 31, 2018.

TECHNICAL FIELD

One or more exemplary embodiments relate to an electronic cigarette control method and an electronic cigarette control device.

BACKGROUND ART

Recently, the demand for alternative methods to overcome the drawbacks of regular cigarettes has been increasing. In detail, the demand for electronic cigarettes is gradually increasing. In addition, as the demand for electronic cigarettes is increasing, functions related to electronic cigarettes are continuously being developed. In particular, functions associated with the types and characteristics of electronic cigarettes are continuously being developed.

DESCRIPTION OF EMBODIMENTS

Technical Problem

One or more exemplary embodiments provide an electronic cigarette control method and an electronic cigarette control device. Also provided is a computer-readable recording medium having recorded thereon a program for executing the method on a computer. The technical objective to be solved is not limited to the technical objectives described above, and other technical objectives may also be present.

Solution to Problem

According to an aspect of the disclosure, an electronic cigarette control device includes: a communicator configured to establish a communication connection with at least one device; and a processor configured to control an electronic cigarette according to a control message with respect to the electronic cigarette, the control message being received from the at least one device through the established communication connection.

According to another aspect of the disclosure, a method of controlling an electronic cigarette control device includes: establishing a communication connection with at least one device; receiving, from the at least one device, a control message with respect to the electronic cigarette through the established communication connection; and controlling the electronic cigarette according to the received control message.

BEST MODE

An aspect of the exemplary embodiments provides an electronic cigarette control device including: a communicator configured to establish a communication connection with at least one device; and a processor configured to control an electronic cigarette according to a control message with respect to the electronic cigarette, the control message being received from the at least one device through the established communication connection.

Another aspect of the exemplary embodiments provides an electronic cigarette control method including: establishing a communication connection with at least one device; receiving, from the at least one device, a control message with respect to the electronic cigarette through the established communication connection; and controlling the electronic cigarette according to the received control message

MODE OF DISCLOSURE

With respect to the terms in the various embodiments of the present disclosure, the general terms which are currently and widely used are selected in consideration of functions of structural elements in the various embodiments of the present disclosure. However, meanings of the terms may be changed according to intention, a judicial precedent, appearance of a new technology, and the like. Also, some terms may be arbitrarily selected by the applicant. In this case, the meaning of the selected terms will be described in the detailed description. Thus, the terms used herein have to be defined based on the meaning of the terms together with the description throughout the specification.

Throughout the specification, it will also be understood that when a component "includes" an element, unless there is another opposite description thereto, it should be understood that the component does not exclude another element but may further include another element. In addition, the terms "-er", "-or", and "module" described in the specification mean units for processing at least one function and operation and can be implemented by hardware components or software components and combinations thereof.

Hereinafter, the present disclosure will now be described more fully with reference to the accompanying drawings, in which embodiments of the present disclosure are shown such that one of ordinary skill in the art may easily work the present disclosure. The disclosure may, however, be embodied in many different forms and should not be construed as limited to the embodiments set forth herein.

Hereinafter, embodiments of the present disclosure will be described in detail with reference to the drawings.

Figure 1:
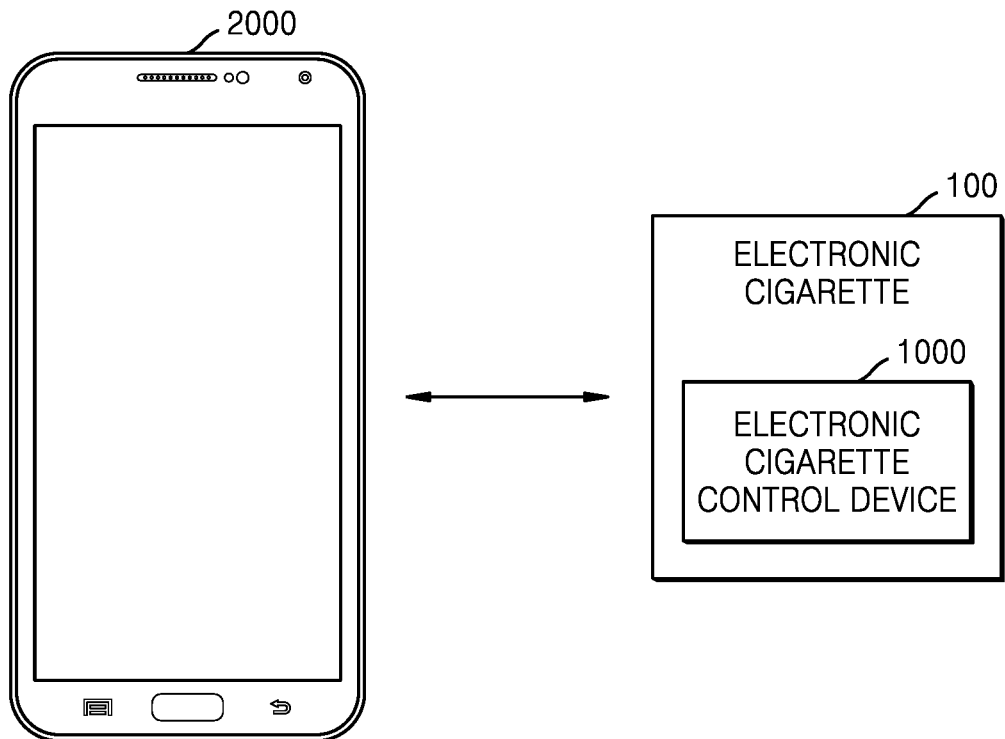
FIG. 1 is a block diagram illustrating an example in which an electronic cigarette control device performs at least one function through a communication connection between a device and the electronic cigarette control device.

FIG. 1 is a block diagram illustrating an example in which an electronic cigarette control device 1000 performs at least one function through a communication connection between a device 2000 and the electronic cigarette control device 1000.

An electronic cigarette 100 according to an exemplary embodiment may collectively refer to smoking related devices that use electricity. For example, as will be described later, a holder and/or cradle may be considered part of the electronic cigarette 100.

The electronic cigarette control device 1000 according to an exemplary embodiment may control the electronic cigarette 100. The electronic cigarette control device 1000 may be included in the electronic cigarette 100. The electronic cigarette control device 1000 may control functions of the electronic cigarette 100. For example, the electronic cigarette control device 1000 may control a communication function, a cleaning function, a storage function, a sensing function, an information reading function, a preheating function, a heater function, a vibration function, an authentication function, or the like, of the electronic cigarette 100, but the function is not limited thereto.

Through a communication, the electronic cigarette control device 1000 may transmit a message to the device 2000 or receive a message from the device 2000. For example, the electronic cigarette control device 1000 may receive, from the device 2000, information about a cigarette that may be inserted into the electronic cigarette 100, which is obtained by the device 2000. Cigarette-related information according to an exemplary embodiment may include a type, a price, a purchase time, or a place of purchase, or the like, but is not limited thereto. According to another example, the electronic cigarette control device 1000 may transmit information about the electronic cigarette 100 to the device 2000. The information about the electronic cigarette 100 according to an exemplary embodiment may include remaining battery power information of the electronic cigarette, information about the number of times of usage of a holder, estimated lifetime information of the electronic cigarette, but is not limited thereto.

The device 2000 may include an apparatus capable of performing a communication function. The device 2000 described in the present specification may include a personal computer (PC), a smart television (TV), a mobile phone, a smart phone, a laptop computer, a digital broadcasting terminal, personal digital assistants (PDA), a portable multimedia player (PMP), a navigation device, a wearable device, or the like, but is not limited thereto.

The electronic cigarette control device 1000 may communicate with the device 2000. For example, the electronic cigarette control device 1000 may establish a communication connection with the device 2000 by using short-range communication such as Bluetooth, a local area network, a remote area network, or the like, but the communication connection is not limited thereto.

In addition, the device 2000 may transmit a control message to the electronic cigarette control device 1000 through communication. In this case, the electronic cigarette control device 1000 may control the electronic cigarette 100 according to a control message received from the device 2000.

The electronic cigarette control device 1000 according to an exemplary embodiment may communicate with at least one device 2000. For example, the electronic cigarette control device 1000 may communicate with two devices. The electronic cigarette control device 1000 may control the electronic cigarette 100 by using a control message received from a first device (not shown) and a control message received from a second device (not shown). For example, the electronic cigarette control device 1000 may control a first function of the electronic cigarette 100 according to a first function control message received from a first device (not shown) and control a second function of the electronic cigarette 100 according to a second function control message received from a second device (not shown) at the same time.

The electronic cigarette 100 according to an exemplary embodiment may be used in generating aerosol. The electronic cigarette 100 may include a component that directly or indirectly involves in generating aerosol. For example, the electronic cigarette 100 may include a holder or a cradle which will be described later with reference to FIG. 3. As another example, the electronic cigarette 100 may include an aerosol-generating device which generates aerosol by using a liquid as a raw material.

Figure 2:
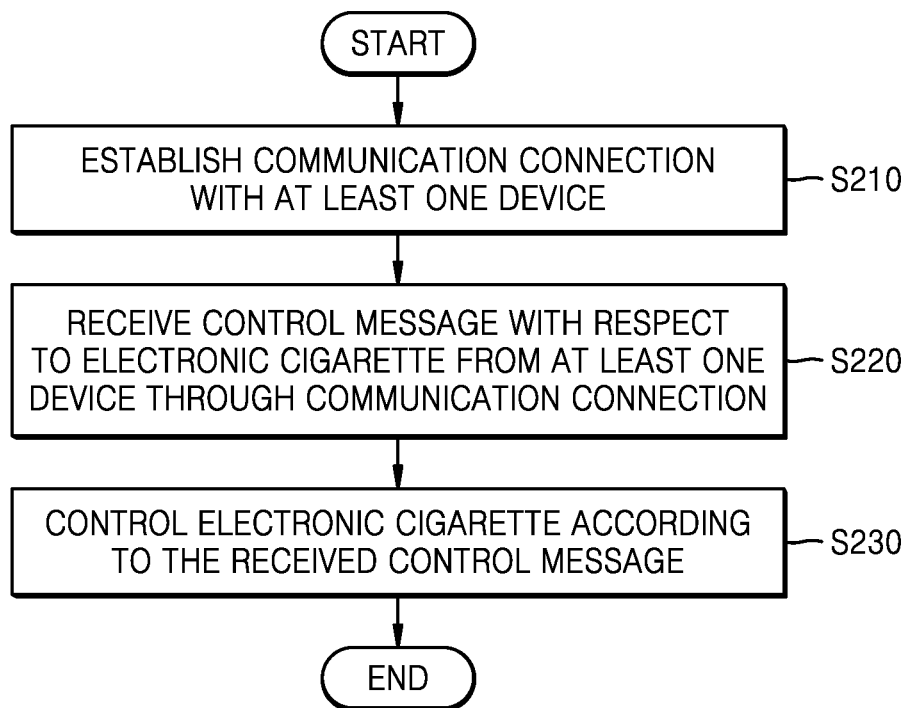
FIG. 2 is a flowchart of an example in which an electronic cigarette control device controls an electronic cigarette through a communication connection established between a device and the electronic cigarette control device.

FIG. 2 is a flowchart of an example in which an electronic cigarette control device 1000 controls an electronic cigarette through a communication connection established between a device 2000 and the electronic cigarette control device 1000.

In operation S210, the electronic cigarette control device 1000 according to an exemplary embodiment may establish a communication connection with at least one device 2000. For example, the electronic cigarette control device 1000 may establish a communication connection with the device 2000 by using short-range communication such as Bluetooth, a local area network, a wide area network, or the like.

The electronic cigarette control device 1000 may perform authentication during a process of establishing a communication connection with the device 2000. The electronic cigarette control device 1000 may establish communication with the device 2000 when authentication is successful, and deny communication with a device (not shown) when authentication fails. Authentication performed during a process of establishing a communication connection will be described later with reference to FIGS. 21 and 22.

In operation S220, the electronic cigarette control device 1000 according to an exemplary embodiment may receive a control message with respect to the electronic cigarette 100 from at least one device 2000 through a communication connection established in operation S210.

The received control message may be used in controlling the electronic cigarette 100. For example, the received control message may be used in controlling a communication function, a cleaning function, a storage function, a sensing function, an information reading function, a preheating function, a heater function, a vibration function, an authentication function, or the like, of the electronic cigarette 100.

The electronic cigarette control device 1000 according to an exemplary embodiment may receive a control message according to a user input with respect to the device 2000. For example, the electronic cigarette control device 1000 may receive a control message for controlling a first function of the electronic cigarette 100 according to a user's touch input obtained during execution of an application executed on the device 2000.

In the present specification, an application is a term meaning application software, and may indicate a program for actually directing a task according to a purpose of using the application to on a computer. An application may broadly refer to software executed by an operating system installed on a device. Thus, an application may include software such as word processors, spread sheets, or web browsers and also compilers or linkers. Also, an application may be abbreviated as 'app.'

The electronic cigarette control device 1000 according to an exemplary embodiment may receive a control message according to a sensor input with respect to the device 2000. For example, the electronic cigarette control device 1000 may receive a control message for controlling a second function of the electronic cigarette 100 according to sensing information obtained by the device 2000, such as images, motions, or positions. For example, when the device 2000 senses a two-dimensional image code, a control message corresponding to the two-dimensional image code may be transmitted from the device 2000 to the electronic cigarette control device 1000. In this case, the electronic cigarette control device 1000 may receive a control message corresponding to the sensed two-dimensional image code.

The electronic cigarette control device 1000 according to an exemplary embodiment may receive a control message according to a user input with respect to the electronic cigarette 100. For example, a control message may be received from the device 2000 according to an input applied via an input device included in the electronic cigarette 100 (for example, a button). For example, pairing between the device 2000 and the electronic cigarette control device 1000 may be performed by using a button included in the electronic cigarette 100.

In operation S230, the electronic cigarette control device 1000 according to an exemplary embodiment may control an electronic cigarette according to the received control message.

For example, according to the control message received in operation S220, a communication function, a cleaning function, a storage function, a sensing function, an information reading function, a preheating function, a heater function, a vibration function, an authentication function, or the like of the electronic cigarette 100 may be controlled. For example, according to a user's touch input obtained during execution of an application executed on the device 2000, a cleaning function, a storage function, a sensing function, an information reading function, a preheating function, a heater function, a vibration function, or the like of the electronic cigarette 100 may be executed or settings of various functions may be modified.

Figure 3:
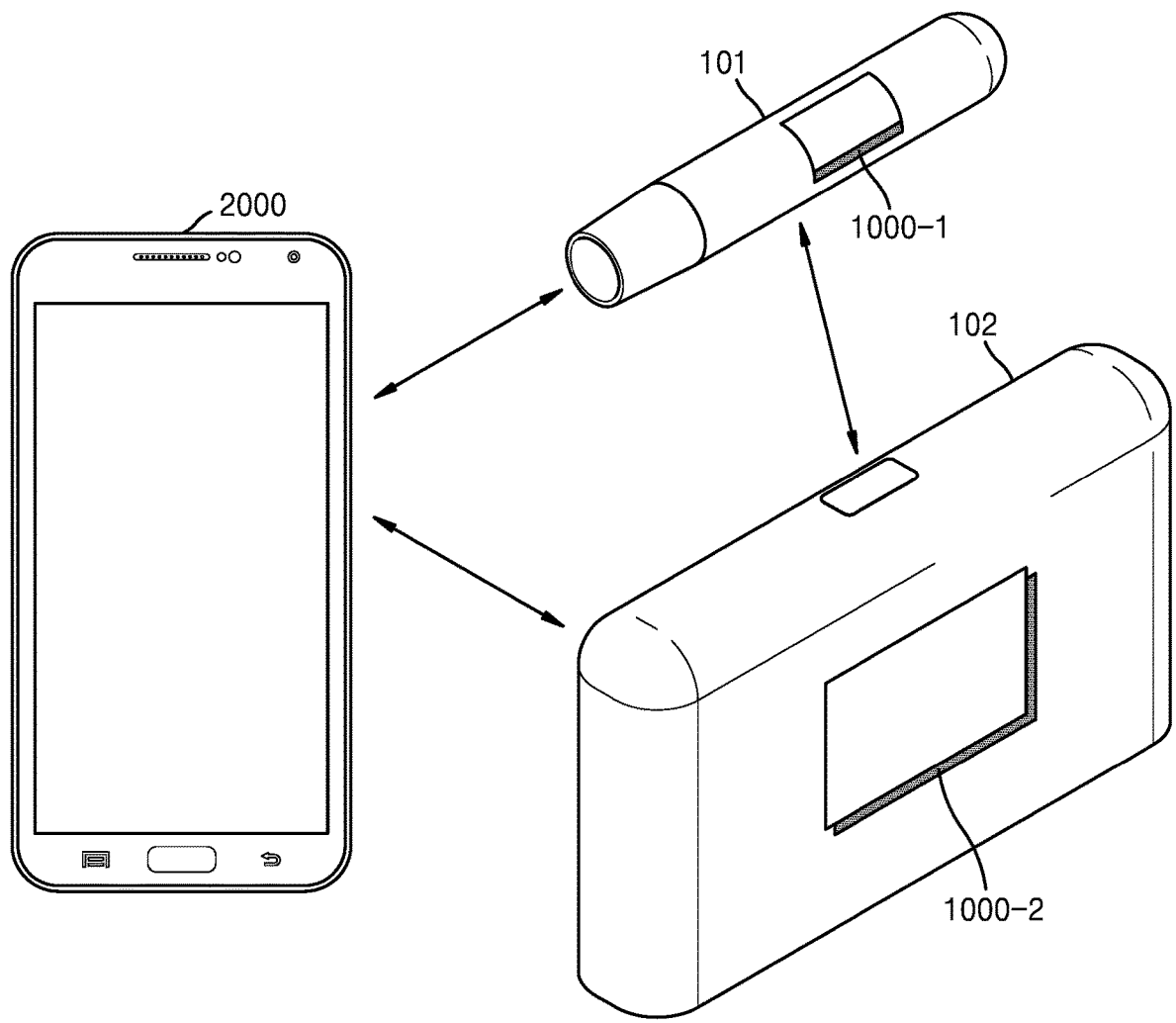
FIG. 3 illustrates an example in which an electronic cigarette control device performs at least one function through a communication connection among a device, a holder and a cradle.

FIG. 3 illustrates an example in which a first electronic cigarette control device 1000-1 and a second electronic cigarette control device 1000-2 perform at least one function through a communication connection among a device 2000, a holder 101, and a cradle 102.

The first electronic cigarette control device 1000-1 may be included in the holder 101, and the second electronic cigarette control device 1000-2 may be included in the cradle 102. The first electronic cigarette control device 1000-1 and the second electronic cigarette control device 1000-2 may be an example of the electronic cigarette control device 1000 described above. The first electronic cigarette control device 1000-1 may control the holder 101, and the second electronic cigarette control device 1000-2 may control the cradle 102. The first electronic cigarette control device 1000-1, the second electronic cigarette control device 1000-2, and the device 2000 may establish a communication connection with one another. In addition, through the communication connection established among the first electronic cigarette control device 1000-1, the second electronic cigarette control device 1000-2, and the device 2000, a function of the holder 101 and a function of the cradle 102 may be performed.

For example, according to a user's touch input obtained during execution of an application executed on the device 2000, data stored in a memory included in the cradle 102 may be transmitted to the holder 101.

As another example, when a control message is transmitted from the device 2000, the transmitted control message may be used in controlling the holder 101 or the cradle 102, depending on whether the holder 101 and the cradle 102 are combined. For example, when the device 2000 has transmitted a control message requesting to start preheating while the holder 101 and the cradle 102 are combined, the holder 101 may start preheating using a battery of the cradle 102, and a preheating lamp included in the cradle 102 may be turned on. However, if the holder 101 and the cradle 102 are separated from each other, the holder 101 may start preheating using a battery of the holder 101, and a preheating lamp included in the holder 101 may be turned on.

Figure 4:
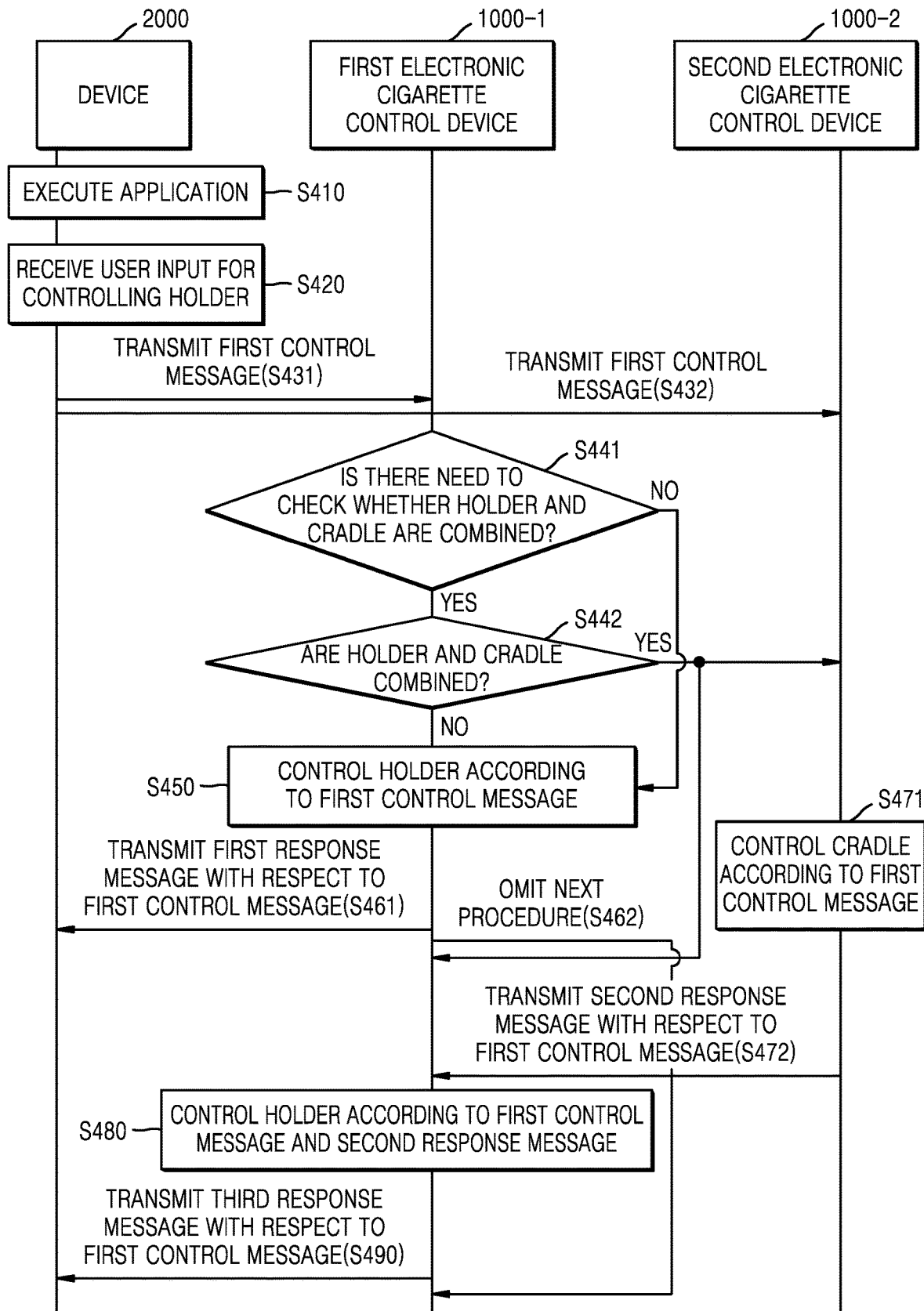
FIG. 4 illustrates an example in which an electronic cigarette control device performs at least one function through a communication connection among a device, a holder, and a cradle.

FIG. 4 illustrates an example in which first electronic cigarette control devices 1000-1 and second electronic cigarette control devices 1000-2 perform at least one function through a communication connection among a device 2000, a holder 101, and a cradle 102.

In operation S410, the device 2000 according to an exemplary embodiment may execute an application. The executed application may be used in controlling the holder 101 and/or the cradle 102. In detail, a control message transmitted during execution of an application may be transmitted to the first electronic cigarette control device 1000-1 included in the holder 101, to control the holder 101, or may be transmitted to the second electronic cigarette control device 1000-2 included in the cradle 102, to control the cradle 102. In FIG. 4, a case in which the holder 101 is controlled according to an exemplary embodiment will be described.

In operation S420, the device 2000 according to an exemplary embodiment receives a user input for controlling the holder 101 according to an application executed in operation S410. The user input may include a cursor motion, a drag & drop, a swipe operation, or the like, via a mouse or touch input. However, the user input is not limited to the above, and any input via which a user may control the device 2000 may be used.

In operation S431, the device 2000 according to an exemplary embodiment transmits a first control message to the first electronic cigarette control device 1000-1. Also, in operation S432, the device 2000 according to an exemplary embodiment transmits a first control message to the second electronic cigarette control device 1000-2. When the device 2000 transmits a control message, the message may be transmitted using a unicasting method with respect to the first electronic cigarette control device 1000-1 or the second electronic cigarette control device 1000-2. Alternatively, the message may be transmitted using a multicasting method to the first electronic cigarette control device 1000-1 and the second electronic cigarette control device 1000-2.

In operation S441, the first electronic cigarette control device 1000-1 according to an exemplary embodiment may parse the first control message to determine whether there is a need to check whether the holder 101 and the cradle 102 are combined, to perform control according to the first control message.

When it is determined in operation S441 that there is a need to check whether the holder 101 and the cradle 102 are combined, in operation S442, the first electronic cigarette control device 1000-1 according to an exemplary embodiment determines whether the holder 101 and the cradle 102 are currently combined.

When it is determined in operation S442 that the holder 101 and the cradle 102 are not combined, in operation S450, the first electronic cigarette control device 1000-1 according to an exemplary embodiment does not wait for a response message from the cradle 102 but controls the holder 101 according to the first control message. In addition, in operation S461, the first electronic cigarette control device 1000-1 according to an exemplary embodiment transmits, to the device 2000, a first response message according to the control of the holder 101 according to the first control message. In addition, in operation S462, the first electronic cigarette control device 1000-1 according to an exemplary embodiment may end an operation related to the first control message.

When it is determined in operation S441 that there is no need to check whether the holder 101 and the cradle 102 are combined, in operation S450, the first electronic cigarette control device 1000-1 according to an exemplary embodiment does not wait for a response message from the cradle 102 but controls the holder 101 according to the first control message. In addition, in operation S461, the first electronic cigarette control device 1000-1 according to an exemplary embodiment transmits, to the device 2000, a first response message according to the control of the holder 101 according to the first control message. In addition, in operation S462, the first electronic cigarette control device 1000-1 according to an exemplary embodiment may end an operation related to the first control message.

When it is determined in operation S442 that the holder 101 and the cradle 102 are combined, in operation S471, the second electronic cigarette control device 1000-2 according to an exemplary embodiment controls the cradle 102 according to the first control message. In operation S472, the second electronic cigarette control device 1000-2 according to an exemplary embodiment transmits, to the first electronic cigarette control device 1000-1, a second response message with respect to the first control message according to a result of controlling the cradle 102 of operation S471. In operation S480, the first electronic cigarette control device 1000-1 controls the holder 101 according to the first control message and the second response message, and in operation S490, the first electronic cigarette control device 1000-1 according to an exemplary embodiment transmits a third response message to the device 2000 based on the control of the holder 101 according to the first control message.

The device 2000 may output a result of controlling according to a user input based on the first response message or the third response message. For example, the device 2000 may display a control result on a screen of the device 2000.

While an exemplary embodiment in which the electronic cigarette control device 1000 operates in the electronic cigarette 100 including the holder 101 and the cradle 102 is described in FIGS. 3 and 4, it will be readily understood by one of ordinary skill in the art that the electronic cigarette control device 1000 may be used regardless of an implementation form of the electronic cigarette 100 (for example, a combination form of the holder 101 and the cradle 102).

Figure 5:
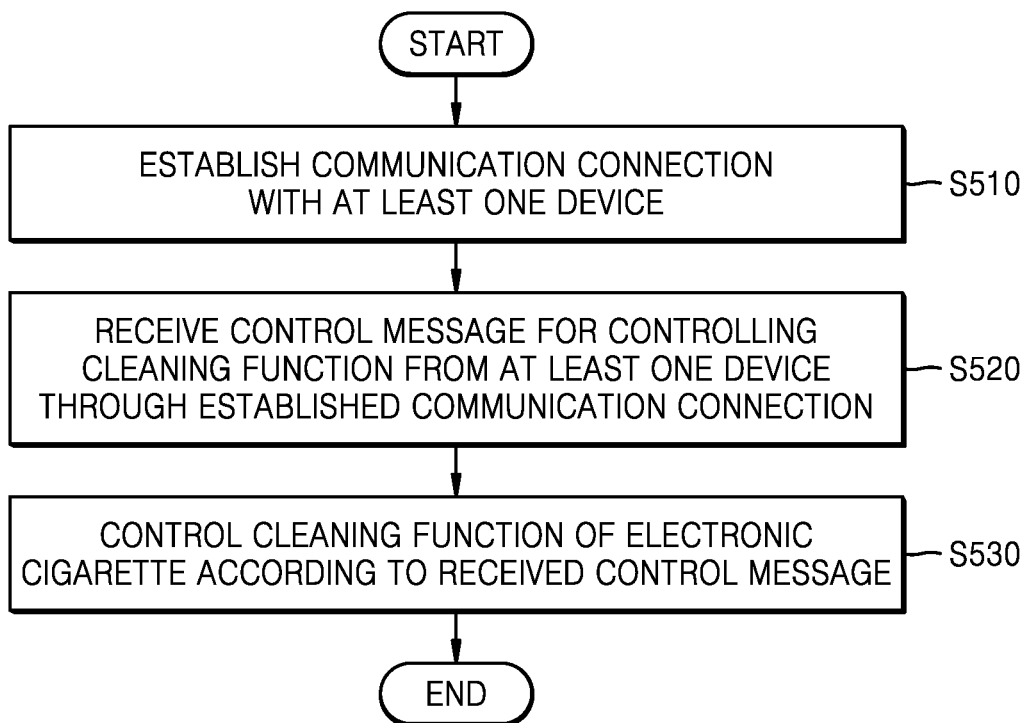
FIG. 5 is a flowchart of an example in which an electronic cigarette control device controls a cleaning function of an electronic cigarette through a communication connection between a device and the electronic cigarette.

FIG. 5 is a flowchart of an example in which an electronic cigarette control device 1000 controls a cleaning function of an electronic cigarette 100 through a communication connection between a device 2000 and the electronic cigarette 100.

In operation S510, the electronic cigarette control device 1000 establishes a communication connection with at least one device 2000. This operation corresponds to S210 described above, and thus, detailed description thereof will be omitted to simplify the overall description.

In operation S520, the electronic cigarette control device 1000 receives a control message for controlling a cleaning function from the at least one device 2000 through a communication connection established in operation S510.

The electronic cigarette 100 according to an exemplary embodiment may include a cleaning function. The cleaning function may include a function of cleaning a preset area of the electronic cigarette 100. For example, the electronic cigarette 100 may perform a cleaning function on a heater. As an example of performing a cleaning function on a heater, the electronic cigarette 100 may perform a cleaning function by heating a heater included in the electronic cigarette 100, but a cleaning function is not limited thereto.

The control message for controlling a cleaning function that is received from the device 2000 may include a control message for controlling operation of the cleaning function of the electronic cigarette 100 (for example, a start of operation of a cleaning function, an end of operation of a cleaning function, etc.) or a control message for making changes to a setting related to a cleaning function (for example, change of a cleaning cycle, change of a setting of a heater temperature when performing cleaning, etc.).

In operation S530, the electronic cigarette control device 1000 controls a cleaning function of the electronic cigarette 100 according to the control message received in operation S520.

The electronic cigarette control device 1000 according to an exemplary embodiment may control operation of a cleaning function. For example, the electronic cigarette control device 1000 may start operation of a cleaning function according to a control message. As another example, the electronic cigarette control device 1000 may end operation of a cleaning function in progress, according to a control message.

The electronic cigarette control device 1000 according to an exemplary embodiment may determine or change a setting related to a cleaning function.

For example, the electronic cigarette control device 1000 may change a cleaning cycle according to a control message. For example, the electronic cigarette control device 1000 may change a cleaning cycle from one day to two days according to a control message according to a user's touch input on the device 2000. As another example, the electronic cigarette control device 1000 may determine a cleaning cycle of fifteen hours according to a control message according to a user's voice input with respect to the device 2000. As another example, the electronic cigarette control device 1000 may change a cleaning cycle from ten times to fifteen times according to a control message according to a user's button input with respect to the device 2000.

As another example, the electronic cigarette control device 1000 may change a setting related to a heater temperature during cleaning, according to a control message. For example, the electronic cigarette control device 1000 may set a heater temperature for cleaning to a particular temperature or change a preset temperature to another temperature, according to a control message. Alternatively, the electronic cigarette control device 1000 may set a heating period of a heater for cleaning, to a particular period, or change a preset period to another period, according to a control message.

Figure 6:
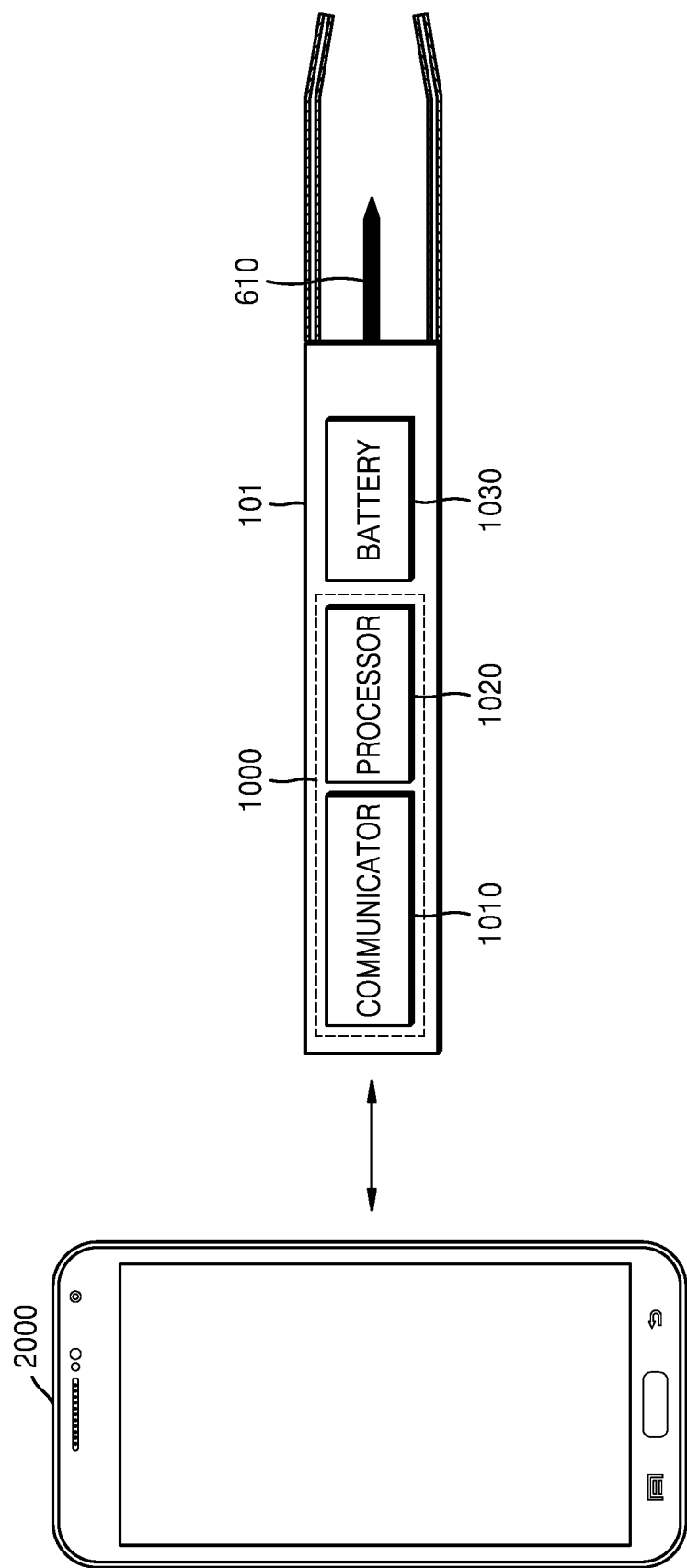
FIG. 6 illustrates an example in which an electronic cigarette control device controls a cleaning function of a holder by using a communication connection between a device and an electronic cigarette.

FIG. 6 illustrates an example in which an electronic cigarette control device 1000 controls a cleaning function of a holder 101 by using a communication connection between a device 2000 and an electronic cigarette 100.

The holder 101 according to an exemplary embodiment may include the electronic cigarette control device 1000, a battery 1030, and a heater 610. Also, the electronic cigarette control device 1000 may include a communicator 1010 and a processor 1020. However, the communicator 1010 and the processor 1020 may not be essential components of the electronic cigarette control device 1000, and a configuration of the electronic cigarette control device 1000 will be described later with reference to FIG. 23.

A control message received by the electronic cigarette control device 1000 in FIG. 6 may be received from the device 2000 or another external device (for example, a cradle).

The holder 101 may include the heater 610. The heater 610 may include a configuration used in generating aerosol. According to an exemplary embodiment, when a cigarette is inserted into the holder 101, the electronic cigarette control device 1000 heats the heater 610. A temperature of an aerosol generating material in the cigarette is raised by the heater 610, and thus aerosol is generated. The generated aerosol is delivered to a user through a filter of the cigarette. However, the electronic cigarette control device 1000 may control the holder 101 to heat the heater 610 even when no cigarette is inserted into the holder 101.

The electronic cigarette control device 1000 according to an exemplary embodiment may perform a cleaning function according to a control message. For example, the electronic cigarette control device 1000 may remove contaminants around the heater 610 by heating the heater 610 to a preset temperature for a preset period. The materials removed by the cleaning function may include arbitrary particles or compounds adhered to or deposited on a surface of the heater 610 while the heater 610 and a cigarette (not shown) contact each other.

The electronic cigarette control device 1000 according to an exemplary embodiment may control the heater 610 to be heated to a second temperature when the cleaning function is being performed. The second temperature may be higher than a first temperature, which is a temperature of the heater 610 when aerosol is generated. The second temperature may include a temperature at which materials deposited on or adhered to a heater may be liberated thermally. Thermal liberation may occur by pyrolysis or carbonization reaction. Thermal liberation may occur by pyrolysis. Pyrolysis may be a process in which chemical compounds are dissolved due to the action of heat.

The electronic cigarette control device 1000 according to an exemplary embodiment may determine or change a period during which a temperature of the heater 610 is maintained at the second temperature, according to a control message. For example, the electronic cigarette control device 1000 may maintain a temperature of the heater at the second temperature for five seconds or longer according to a control message, and thermally remove materials adhered to the heater during the period maintained at the second temperature. As another example, the electronic cigarette control device 1000 may set a period during which a temperature of the heater is maintained at the second temperature, to between five seconds to sixty seconds, according to a control message.

The electronic cigarette control device 1000 according to an exemplary embodiment may raise a temperature of the heater 610 above the temperature set according to a control message when performing a cleaning function. For example, the electronic cigarette control device 1000 may determine a temperature of the heater 610 to be 430° C. or higher, 480° C. or higher, 550° C. or higher, 600° C. or higher, or 800° C. or higher, according to a control message.

The electronic cigarette control device 1000 according to an exemplary embodiment may determine or change a cleaning cycle according to a control message. The electronic cigarette control device 1000 may perform a cleaning function periodically according to a cycle determined according to a control message.

For example, when a user input of determining a cleaning cycle to be two days is obtained from the device 2000, the device 2000 may transmit a control message requesting to set a cleaning period to two days, and the electronic cigarette control device 1000 may determine a cleaning period of the holder 101 to be two days.

A cleaning cycle according to an exemplary embodiment may be determined within a preset range. For example, a cleaning cycle may be determined between ten minutes and thirty days according to a user input. As another example, a cleaning cycle may be determined to be between one smoking time and 100 smoking times, according to a user input.

Figure 7:
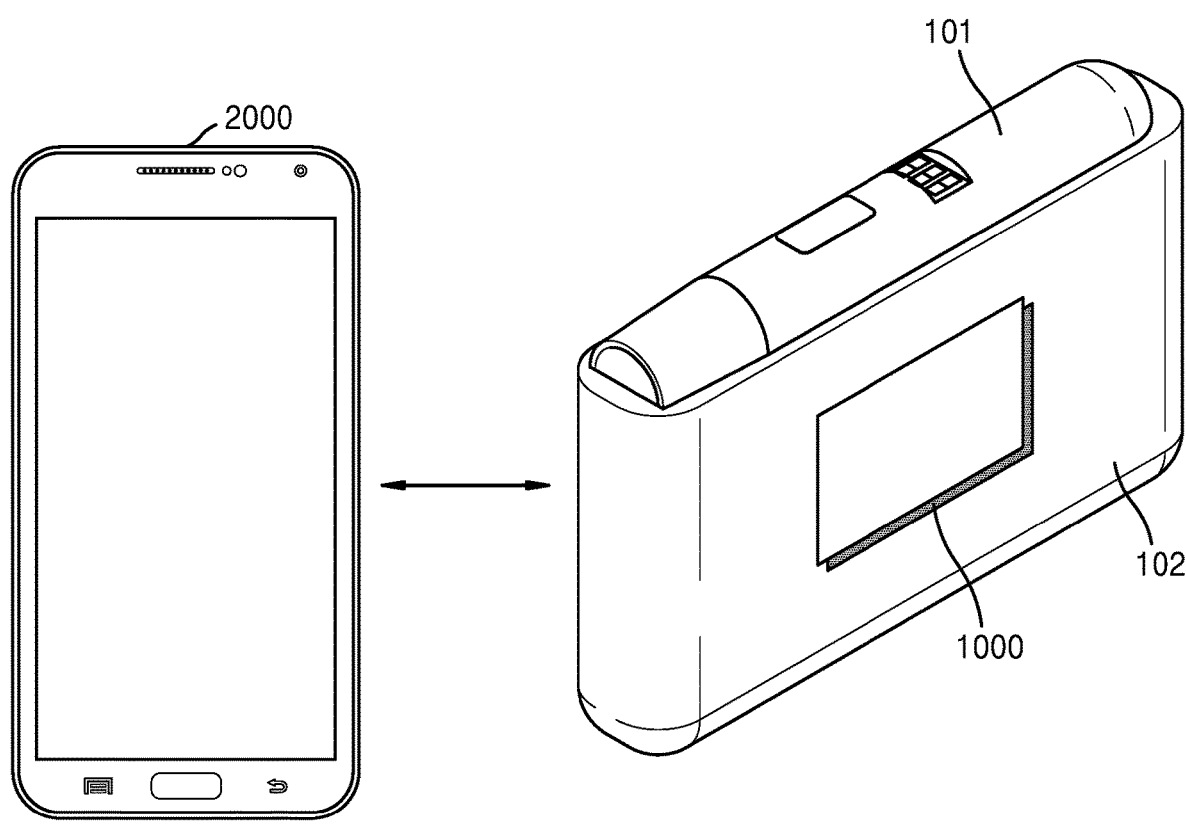
FIG. 7 illustrates an example in which an electronic cigarette control device controls a cleaning function by controlling a holder or a cradle by using a communication connection between a device and an electronic cigarette.

FIG. 7 illustrates an example in which an electronic cigarette control device 1000 controls a cleaning function by controlling a holder 101 or a cradle 102 by using a communication connection between a device 2000 and an electronic cigarette 100.

A cleaning function may be performed by the holder 101 according to the control by the electronic cigarette control device 1000 included in the cradle 102.

For example, when the electronic cigarette control device 1000 included in the cradle 102 receives a control message requesting to set a cleaning cycle to three days, the electronic cigarette control device 1000 may control the holder 101 such that a cleaning period of the holder 101 is set to three days. In this case, the electronic cigarette control device 1000 may control the holder 101 via wire or wireless communication between the holder 101 and the cradle 102.

Figure 8:
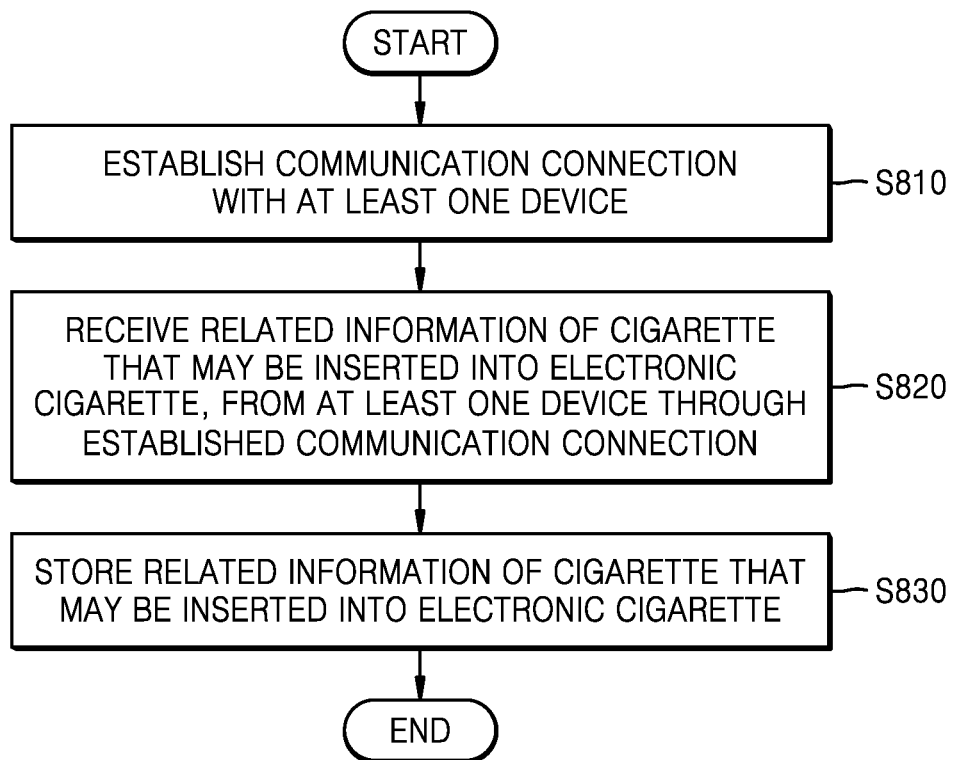
FIG. 8 is a flowchart of an example in which an electronic cigarette control device obtains information about a cigarette that may be inserted into an electronic cigarette by using a communication connection between a device and the electronic cigarette.

FIG. 8 is a flowchart of an example in which an electronic cigarette control device 1000 obtains information about a cigarette that may be inserted into an electronic cigarette 100 by using a communication connection between a device 2000 and the electronic cigarette 100.

The electronic cigarette control device 1000 according to an exemplary embodiment may receive the obtained information from the device 2000 through a communication connection and store the information. Referring to the present drawing, an exemplary embodiment in which the electronic cigarette control device 1000 receives and stores information about a cigarette that may be inserted into the electronic cigarette 100 will be described.

In operation S810, the electronic cigarette control device 1000 establishes a communication connection with at least one device 2000. This operation corresponds to S210 described above, and thus, detailed description thereof will be omitted to simplify the overall description.

In operation S820, the electronic cigarette control device 1000 receives information about a cigarette that may be inserted into the electronic cigarette 100 from the at least one device 2000 through a communication connection established in operation S810.

For example, the electronic cigarette control device 1000 may receive, from the device 2000, information about a cigarette that may be inserted into the electronic cigarette 100.

Information about the cigarette may include, a type, price, purchase date, purchase time, place of purchase, manufacturer, type of incense, and raw materials (e.g., the variety of leaf tobacco), various characteristics (physical characteristics, chemical characteristics, appearance, flavors, etc.), relevant notes (e.g., notes that a user has previously written about the product), the place of origin (e.g., place of origin of the product, place of origin of raw materials, etc.), types of substances, contents by substances, sales volume (e.g. sales ranking, domestic sales of this year, overseas sales of last year, etc.), and colors (e.g. surface color, case color, color of the raw materials, etc.) of the cigarette.

Information received by the electronic cigarette control device 1000 from the device 2000 may be obtained by the device 2000 by using various methods.

The device 2000 according to an exemplary embodiment may obtain information about a cigarette that may be inserted into the electronic cigarette 100, through image recognition.

For example, the device 2000 may obtain, from an image-type code, information about a cigarette that may be inserted into the electronic cigarette 100. In detail, the device 2000 may obtain information about a cigarette that may be inserted into the electronic cigarette 100, by recognizing a QR (quick response) code or a bar code.

As another example, the device 2000 may obtain information about a cigarette that may be inserted into the electronic cigarette 100, through recognition of characters. In detail, the device 2000 may obtain information about a cigarette that may be inserted into the electronic cigarette 100, by recognizing characters indicating the name of a cigarette on a cigarette case. In detail, the device 2000 may specify a type of a cigarette that may be inserted into the electronic cigarette 100 by recognizing characters indicating the name of the cigarette on a cigarette case and obtain cigarette-information about the specified cigarette.

The information about the cigarette obtained by the device 2000 through image recognition may be expected to be inserted into the electronic cigarette 100.

In operation S830, the electronic cigarette control device 1000 may store the information about the cigarette received in operation S820. For example, the electronic cigarette control device 1000 may store the information about the cigarette received in operation S820, in a memory in the electronic cigarette 100.

When information about a cigarette is received a plurality of times, the electronic cigarette control device 1000 may sequentially store the information about the cigarette in a memory in the electronic cigarette 100. When the electronic cigarette control device 1000 has obtained a plurality of pieces of information about the cigarette from the device 2000, the information about the cigarette that is obtained most recently may be determined as information to be used, and store, transmit, output or display the determined information of the cigarette. For example, the electronic cigarette control device 1000 may transmit the determined information of the cigarette that is expected to be used, to the device 2000. In this case, the device 2000 may display the information of the cigarette that is expected to be used, after receiving from the electronic cigarette control device 1000.

In operation S820, the information about the cigarette may be output from the electronic cigarette 100. For example, the information of the cigarette expected to be used may be displayed on a display (not shown) included in the electronic cigarette 100.

Figure 9:
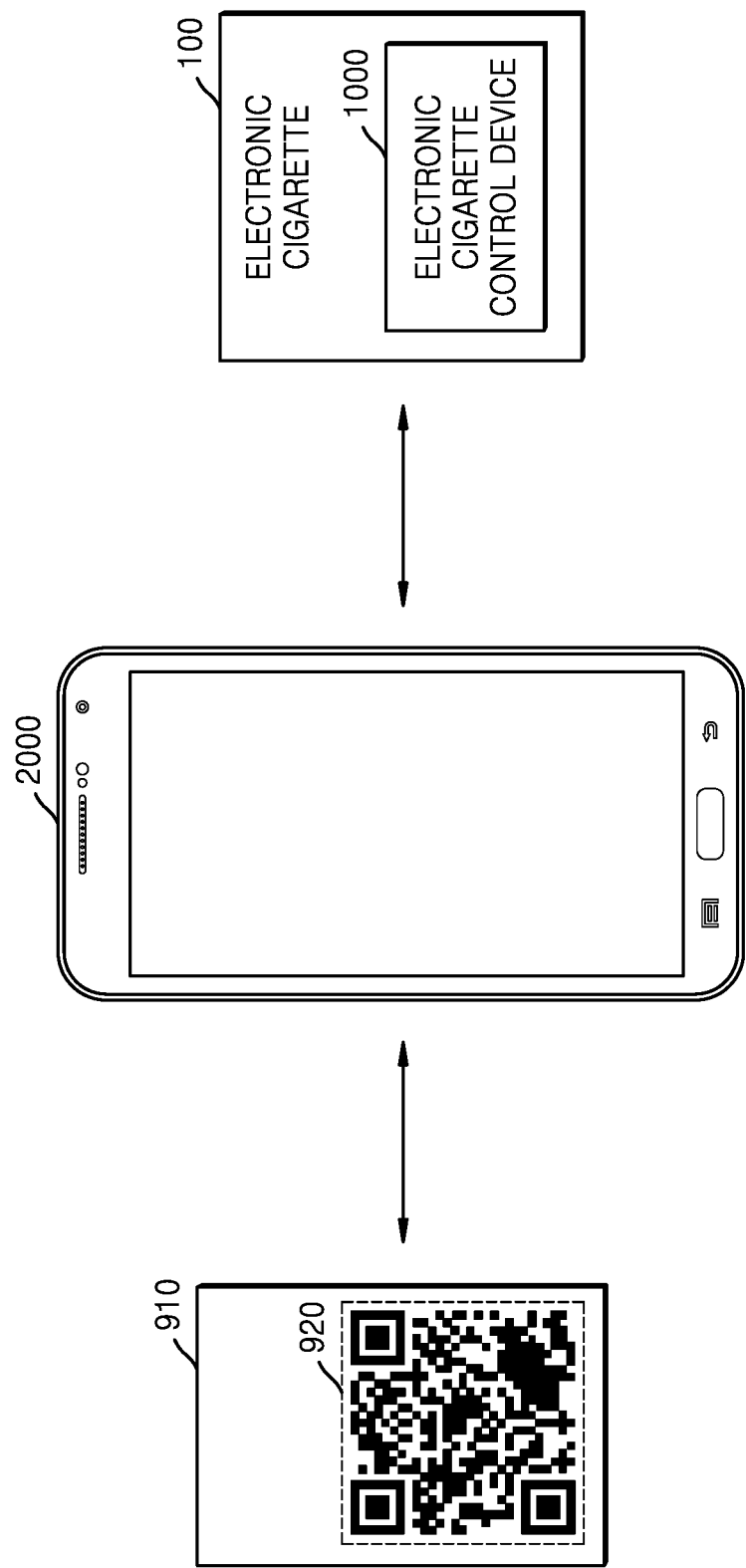
FIG. 9 is a flowchart of an example in which an electronic cigarette control device obtains information about a cigarette, obtained from a two-dimensional image-type code by using a communication connection between a device and an electronic cigarette.

FIG. 9 is a flowchart of an example in which an electronic cigarette control device 1000 obtains information about a cigarette, which is obtained from an image-type code by using a communication connection between a device 2000 and an electronic cigarette 100.

According to an exemplary embodiment, by recognizing a QR code disclosed on a cigarette case, the device 2000 may obtain information about a cigarette that may be inserted into the electronic cigarette 100.

For example, the device 2000 may recognize a QR code by using an image sensor (for example, a camera) included in the device 2000 and transmit information obtained from the QR code, to the electronic cigarette control device 1000.

As another example, the device 2000 may recognize a QR code by using an image sensor included in the device 2000, and obtain, from a server, additional information corresponding to the information obtained from the QR code, and transmit a portion or all of the information obtained from the QR code and the information from the server, to the electronic cigarette control device 1000.

The electronic cigarette control device 1000 may receive, from the device 2000, the information about the cigarette, obtained based on an image-type code, and store the information. In addition, when there is a request from the device 2000, the electronic cigarette control device 1000 may transmit, to the device 2000, the information about the cigarette, received from the device 2000. For example, when there are a plurality of pieces of information about a cigarette, received from the device 2000, the electronic cigarette control device 1000 may transmit information about a cigarette, received most recently, to the device 2000.

Figure 10:
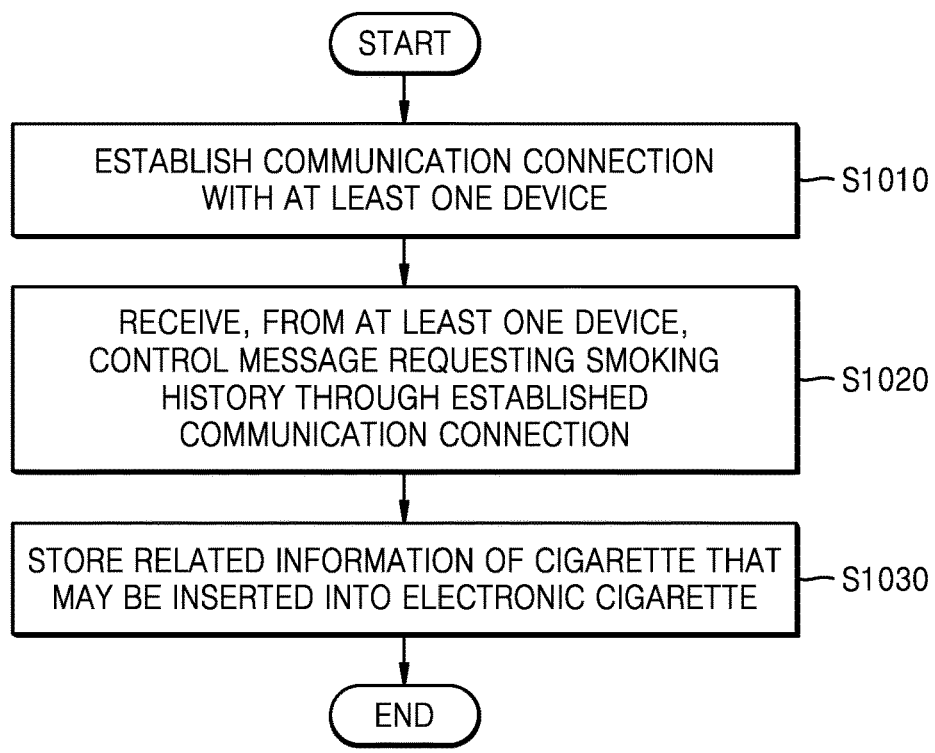
FIG. 10 is a flowchart of an example in which an electronic cigarette control device transmits a message indicating a smoking history to at least one device by using a communication connection between the at least one device and an electronic cigarette.

FIG. 10 is a flowchart of an example in which an electronic cigarette control device 1000 transmits a message indicating a smoking history to at least one device 2000 by using a communication connection between the at least one device 2000 and an electronic cigarette 100.

In operation S1010, the electronic cigarette control device 1000 establishes a communication connection with at least one device 2000. This operation corresponds to S210 described above, and thus, detailed description thereof will be omitted to simplify the overall description.

In operation S1020, the electronic cigarette control device 1000 receives, from the at least one device 2000, a control message for requesting a smoking history through the communication connection established in operation S1010. However, the above operation may be omitted according to embodiments as will be described later.

The smoking history may include records related to smoking using the electronic cigarette 100. For example, the smoking history may include records related to smoking using the electronic cigarette 100, such as a smoking time, a smoking location, a duration of each smoking, a number of times of smoking (e.g., the number of times of smoking per hour, the number of times of smoking in succession, the number of times of smoking per day), types of cigarettes used for smoking, and the like.

In operation S1030, the electronic cigarette control device 1000 transmits a message indicating a smoking history of the electronic cigarette 100, to at least one device 2000.

The electronic cigarette control device 1000 according to an exemplary embodiment may transmit a message indicating a smoking history to the device 2000 according to a request from the device 2000. For example, smoking history information stored in a memory in the electronic cigarette 100 may be transmitted, according to a request from the device 2000, to the device 2000 through a communication connection established in operation S1010.

The electronic cigarette control device 1000 according to an exemplary embodiment may transmit a message indicating a smoking history, to the device 2000 each time the smoking history is updated. Regardless of a request from the device 2000, each time a smoking history is updated according to operation of the electronic cigarette 100, the electronic cigarette control device 1000 may transmit a message indicating the updated smoking history to the device 2000.

The electronic cigarette control device 1000 according to an exemplary embodiment may transmit a message indicating a smoking history to the device 2000 at each preset cycle. Regardless of a request from the device 2000, the electronic cigarette control device 1000 may transmit a message indicating an updated smoking history at each preset cycle (for example, 10 seconds, 1 minute, 1 hour, etc.) to the device 2000.

Figure 11:
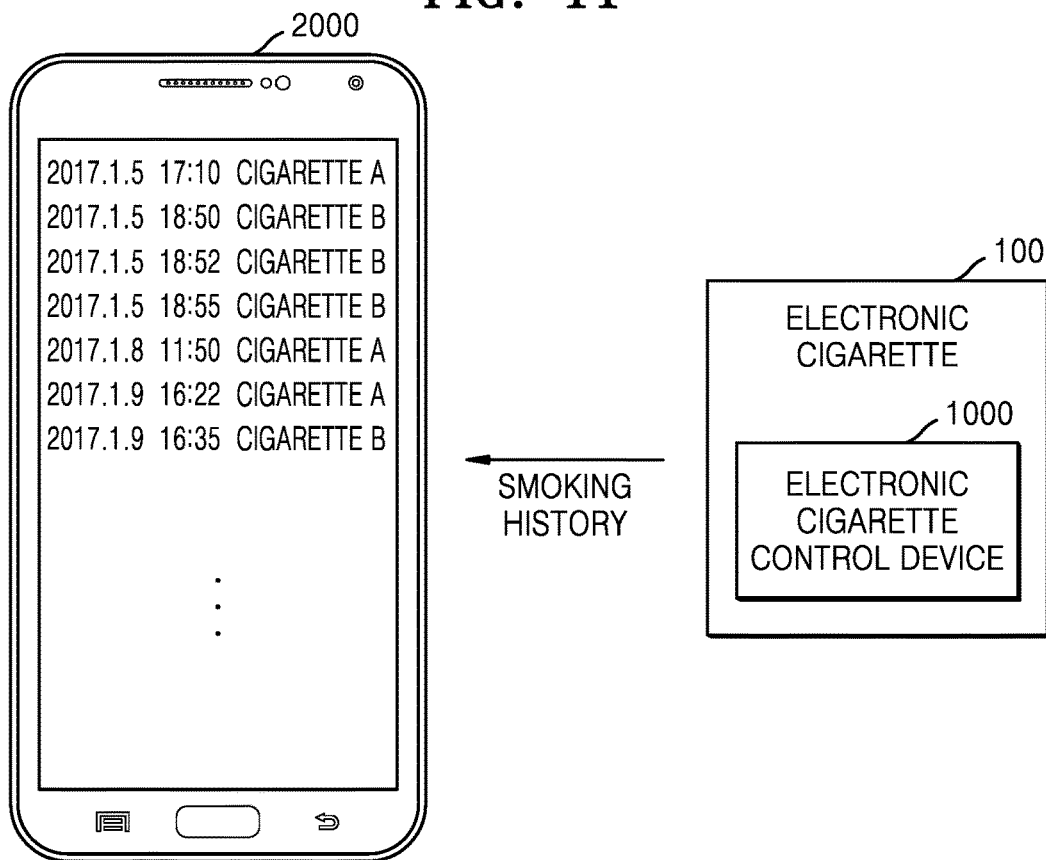
FIG. 11 illustrates an example in which an electronic cigarette control device transmits a message indicating a smoking history to at least one device by using a communication connection between the at least one device and an electronic cigarette.

FIG. 11 illustrates an example in which an electronic cigarette control device 1000 transmits a message indicating a smoking history to at least one device 2000 by using a communication connection between the at least one device 2000 and an electronic cigarette 100.

As illustrated in FIG. 11, the electronic cigarette control device 1000 may transmit a message indicating a smoking history to the device 2000. In this case, the device 2000 may display a portion of or all of the received smoking history. In FIG. 11, although a date of smoking, a smoking time, and a type of a cigarette used for smoking are displayed in relation to a smoking history, the smoking history is not limited thereto.

Figure 12:
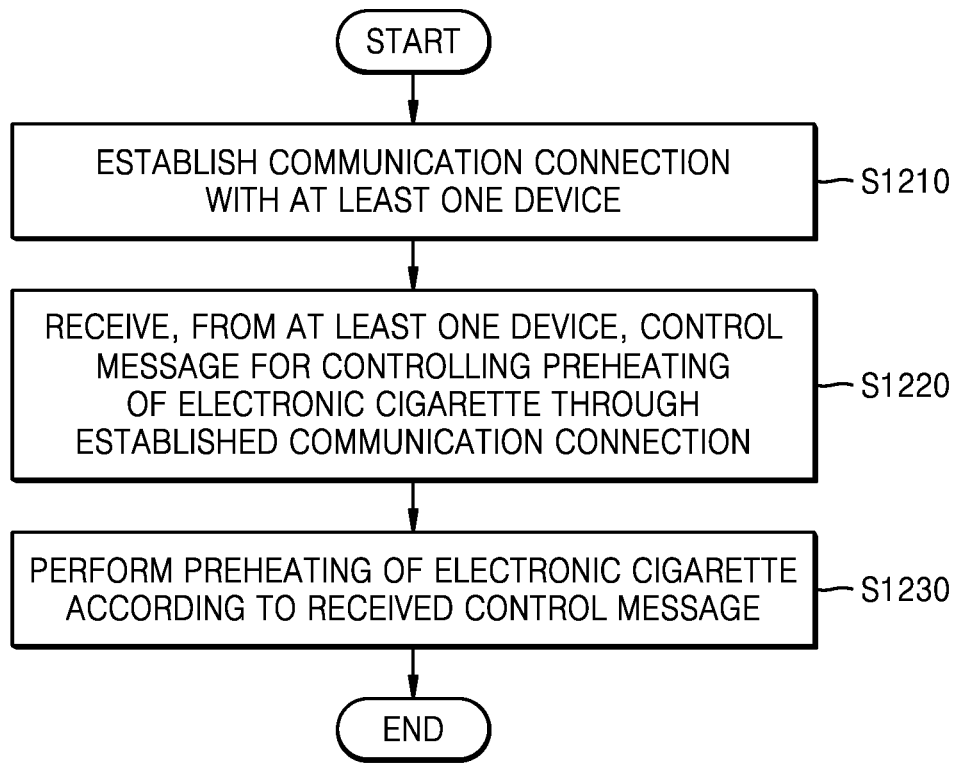
FIG. 12 is a flowchart of an example in which an electronic cigarette control device controls a preheating function of an electronic cigarette by using a communication connection established between a device and the electronic cigarette.

FIG. 12 is a flowchart of an example in which an electronic cigarette control device 1000 controls a preheating function of an electronic cigarette 100 by using a communication connection between a device 2000 and the electronic cigarette 100.

In operation S1210, the electronic cigarette control device 1000 establishes a communication connection with at least one device 2000. This operation corresponds to S210 described above, and thus, detailed description thereof will be omitted to simplify the overall description.

In operation S1220, the electronic cigarette control device 1000 receives a control message for controlling a preheating function of the electronic cigarette 100 from the at least one device 2000 through the communication connection established in operation S1210.

The control message for controlling a preheating function may be used in controlling the preheating function. For example, the control message for controlling the preheating function may include a message requesting to start preheating or to end preheating. As another example, the control message for controlling a preheating function may include a message used in determining or changing a preheating temperature, a preheating time (for example, a preheating mode maintaining period), or the like.

The control message for controlling a preheating function may be received from the device 2000 according to a user input. For example, when a user input of requesting to start preheating is applied to the device 2000, the electronic cigarette control device 1000 may receive, from the device 2000, a control message requesting to start preheating.

In operation S1230, the electronic cigarette control device 1000 performs preheating of the electronic cigarette 100 according to the control message received in operation S1220.

The electronic cigarette control device 1000 according to an exemplary embodiment may start preheating of the electronic cigarette 100 according to a control message requesting to start preheating or end preheating of the electronic cigarette 100 according to a control message requesting to end preheating.

The electronic cigarette control device 1000 according to an exemplary embodiment may determine or change a setting related to preheating of the electronic cigarette 100 according to a control message requesting to determine or change the setting related to preheating. For example, the electronic cigarette control device 1000 may determine or change a preheating temperature, a preheating time or the like, according to a control message for controlling a preheating function.

The electronic cigarette 100 may operate in a preheating mode before operating in a smoking mode in which aerosol is generated. The electronic cigarette control device 1000 according to an exemplary embodiment may control the electronic cigarette 100 to operate in a smoking mode or a preheating mode. The electronic cigarette control device 1000 may control the electronic cigarette 100 to operate in a preheating mode to perform preheating of a heater, or may control the electronic cigarette 100 to operate in a smoking mode to perform a smoking operation (for example, heating until a heater temperature reaches 500° C. or higher). A temperature of the heater in the preheating mode may be lower than that of the heater in the smoking mode.

Figure 13:
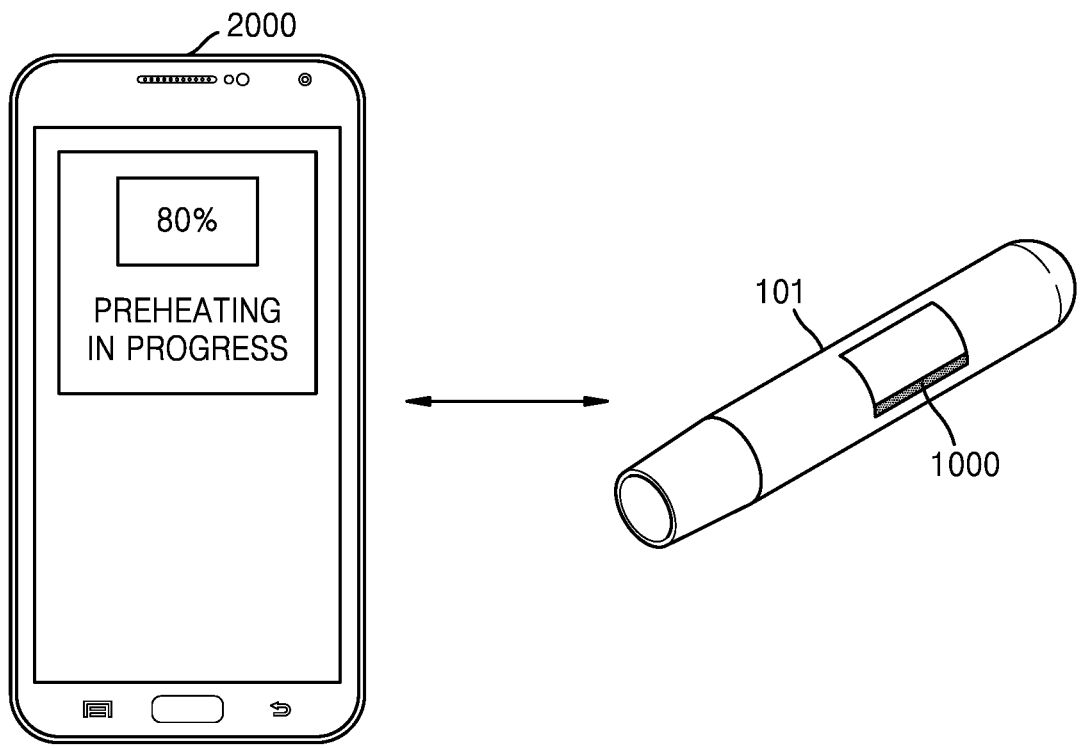
FIG. 13 illustrates an example in which an electronic cigarette control device controls a preheating function of a holder by using a communication connection between a device and an electronic cigarette and transmits a message indicating a preheating status.

FIG. 13 illustrates an example in which an electronic cigarette control device 1000 controls a preheating function of a holder 101 by using a communication connection between a device 2000 and an electronic cigarette 100 and transmits a message indicating a preheating status.

The electronic cigarette control device 1000 according to an exemplary embodiment may control a preheating function according to a control message received from the device 2000. For example, the electronic cigarette control device 1000 may control the electronic cigarette 100 to start preheating of the electronic cigarette 100 according to a control message requesting to start preheating or end preheating of the electronic cigarette 100 according to a control message requesting to end preheating.

The electronic cigarette control device 1000 according to an exemplary embodiment may transmit, to the device 2000, a response message related to preheating. For example, the electronic cigarette control device 1000 may transmit, to a device, a response message indicating a preheating-related situation such as a start of preheating, progress of preheating, or completion of preheating. As example, the electronic cigarette control device 1000 may transmit, to a device, a response message requesting to notify a preheating-related situation such as a start of preheating, progress of preheating, or completion of preheating. As another example, the electronic cigarette control device 1000 may transmit, to a device, a response message indicating a status of progress of preheating.

The device 2000 according to an exemplary embodiment may output a response according to a response message received from the electronic cigarette control device 1000. For example, the device 2000 may display a status of progress of preheating (for example, whether preheating is started, the degree the progress of preheating, whether preheating is completed, or the like), according to a received response message. As another example, the device 2000 may output an alarm notifying completion of preheating, according to a received response message, by vibration or sound.

Figure 14:
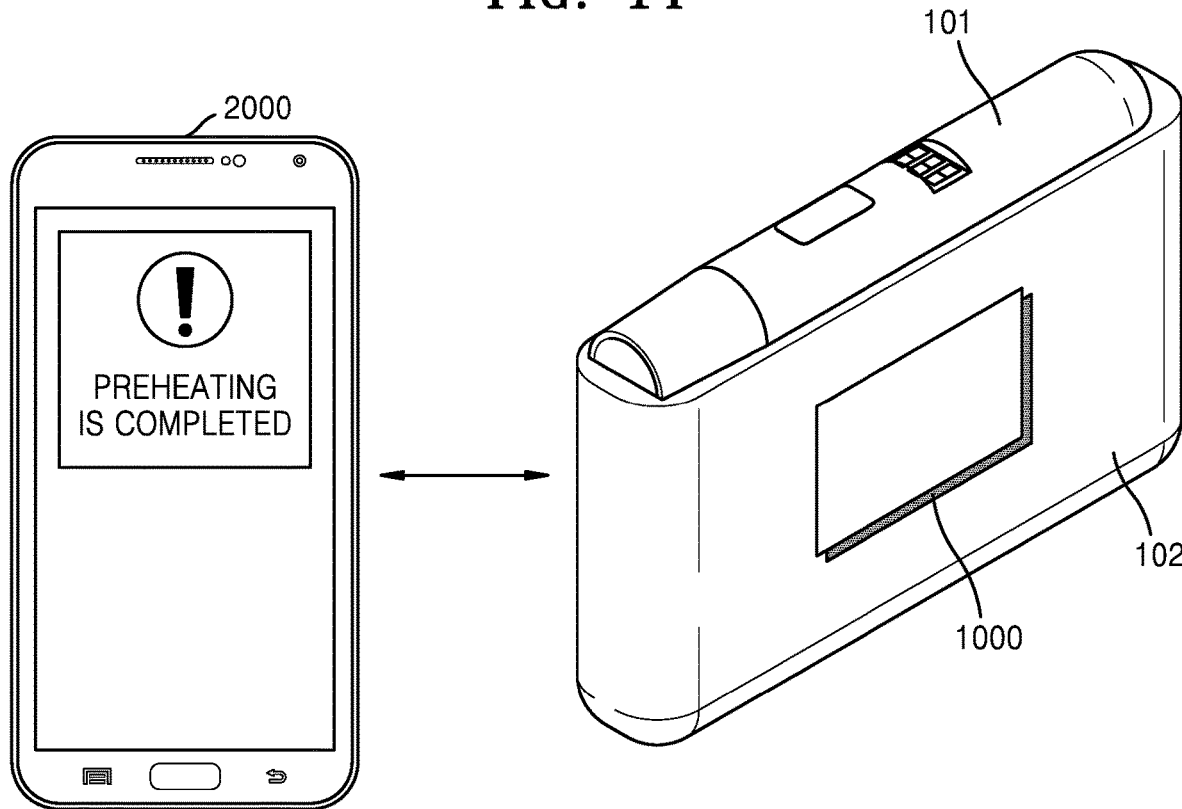
FIG. 14 illustrates an example in which an electronic cigarette control device controls a preheating function by controlling a holder or a cradle by using a communication connection between a device and an electronic cigarette and transmits a message indicating a preheating status.

FIG. 14 illustrates an example in which an electronic cigarette control device 1000 controls a preheating function by controlling a holder 101 or a cradle 102 by using a communication connection between a device 2000 and an electronic cigarette 100 and transmits a message indicating a preheating status.

A preheating function may be performed by the holder 101 according to the control by the electronic cigarette control device 1000 included in the cradle 102.

For example, when the electronic cigarette control device 1000 included in the cradle 102 receives a control message requesting to start preheating, the electronic cigarette control device 1000 may control the holder 101 to start preheating. In this case, the electronic cigarette control device 1000 may control the holder 101 through wire or wireless communication between the holder 101 and the cradle 102.

As another example, when the electronic cigarette control device 1000 included in the cradle 102 receives a control message requesting to set a maximum maintaining period of a preheating mode to 1 minute, the electronic cigarette control device 1000 may control the holder 101 such that the maximum maintaining period of a preheating mode of the holder 101 is set to 1 minute. In this case, the electronic cigarette control device 1000 may control the holder 101 through wire or wireless communication between the holder 101 and the cradle 102.

Figure 15:
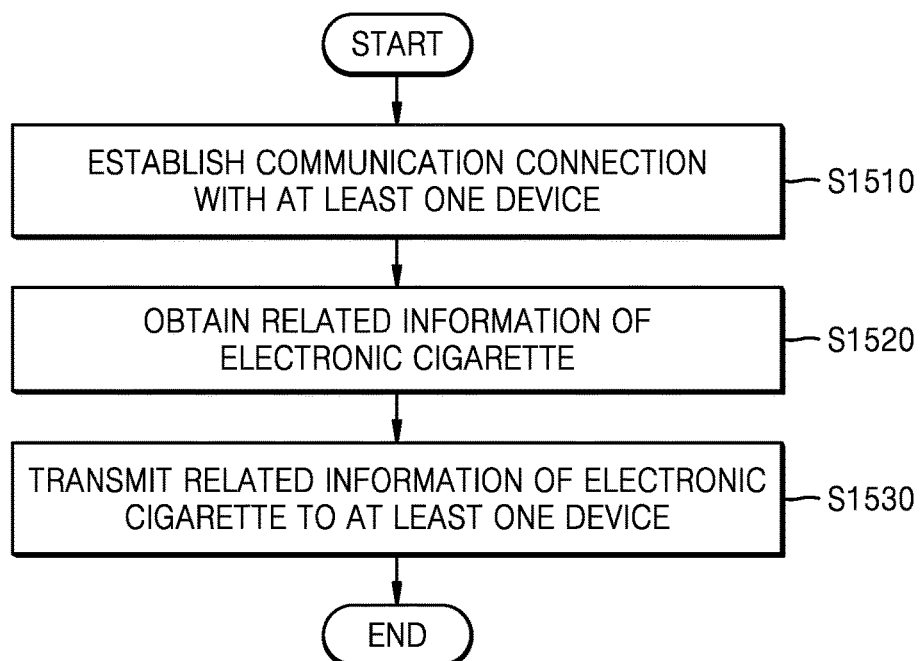
FIG. 15 is a flowchart of an example in which an electronic cigarette control device transmits cigarette-information about an electronic cigarette to at least one device by using a communication connection between the at least one device and the electronic cigarette.

FIG. 15 is a flowchart of an example in which an electronic cigarette control device 1000 transmits cigarette-information about an electronic cigarette 100 to at least one device 2000 by using a communication connection between the at least one device 2000 and the electronic cigarette 100.

In operation S1510, the electronic cigarette control device 1000 establishes a communication connection with the at least one device 2000. This operation corresponds to S210 described above, and thus, detailed description thereof will be omitted to simplify the overall description.

In operation S1520, the electronic cigarette control device 1000 may obtain information about the electronic cigarette 100. The information about the electronic cigarette 100 according to an exemplary embodiment may include device information of the electronic cigarette 100 or usage information of the electronic cigarette 100. For example, information about the electronic cigarette 100 may include, without limitation, information about a battery of the electronic cigarette 100 (e.g., remaining battery power information, battery charging frequency information, battery usage period information, available battery usage time information, puff count information based on battery level, information about estimated remaining lifetime of battery, etc.), holder 101 related information (e.g., information about the number of times of using the holder 101, information about the number of times of using the holder 101 in the last month, information about a usage period of the holder 101, information about a place of purchase of the holder 101, information about a place of origin of the holder 101, information about estimated remaining lifetime of the holder 101, information about a battery of the holder 101, etc.), cradle 102 related information (e.g., information about the number of times of using the cradle 102, information about the number of times of using the cradle 102 in the last month, information about a usage period of the cradle 102, information about a place of purchase of the cradle 102, information about a place of origin of the cradle 102, information about estimated remaining lifetime of the cradle 102, information about a battery of the cradle 102, etc.), usage information of the electronic cigarette 100 (e.g., information about the number of times of using the electronic cigarette 100, information about the number of times of using the electronic cigarette 100 in the last month, information about estimated remaining lifetime of the electronic cigarette 100, information about a battery of the electronic cigarette 100, etc.), and various setting information of the electronic cigarette 100 (e.g., temperature-related setting information, vibration-related setting information, cleaning-related setting information, communication-related setting information, notification-related setting information, charging-related setting information, etc.).

In operation 1530, the electronic cigarette control device 1000 may transmit information about the electronic cigarette 100 to at least one device 2000.

The electronic cigarette control device 1000 according to an exemplary embodiment may transmit the information about the electronic cigarette 100 to the device 2000 according to a request from the device 2000. For example, information about the electronic cigarette 100 stored in a memory in the electronic cigarette 100 may be transmitted, according to a request from the device 2000, to the device 2000 through a communication connection.

The electronic cigarette control device 1000 according to an exemplary embodiment may transmit the information about the electronic cigarette 100 to the device 2000 according to updates of the information about the electronic cigarette 100. For example, each time information about the electronic cigarette 100 is updated, the electronic cigarette control device 1000 may transmit updated information about the electronic cigarette 100 to the device 2000 regardless of a request from the device 2000. As another example, when remaining battery power is reduced to a preset level or lower, information about the remaining battery power may be transmitted to the device 2000.

The electronic cigarette control device 1000 according to an exemplary embodiment may transmit information about the electronic cigarette 100 to the device 2000 at each preset cycle. Regardless of a request from the device 2000, the electronic cigarette control device 1000 may transmit, to the device 2000, updated information about the electronic cigarette 100 at each preset cycle (for example, 10 seconds, 1 minute, 1 hour, etc.).

Figure 16:
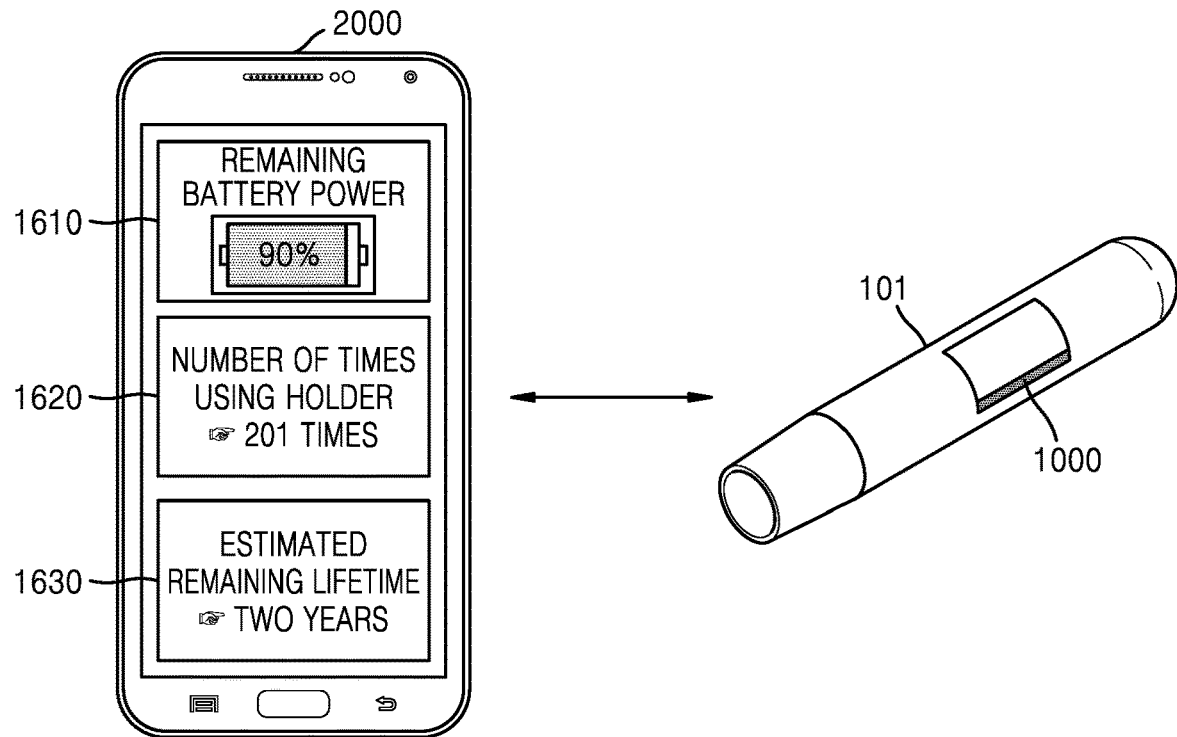
FIG. 16 illustrates an example in which an electronic cigarette control device transmits cigarette-information about an electronic cigarette to at least one device by using a communication connection between the at least one device and the electronic cigarette.

FIG. 16 illustrates an example in which the electronic cigarette control device 1000 transmits information about the electronic cigarette 100 to at least one device 2000 by using a communication connection between the at least one device 2000 and the electronic cigarette 100.

The electronic cigarette control device 1000 according to an exemplary embodiment may transmit, to the device 2000, battery-cigarette-related information. In this case, the device 2000 may display remaining battery power on a first window 1610 based on information obtained from the electronic cigarette control device 1000.

The electronic cigarette control device 1000 according to an exemplary embodiment may transmit, to the device 2000, information related to the holder 101. In this case, the device 2000 may display the number of times of using the holder 101 on a second window 1620 based on information obtained from the electronic cigarette control device 1000.

The electronic cigarette control device 1000 according to an exemplary embodiment may transmit, to the device 2000, estimated remaining lifetime information. In this case, the device 2000 may display the estimated remaining lifetime information on a third window 1630 based on the information obtained from the electronic cigarette control device 1000.

Figure 17:
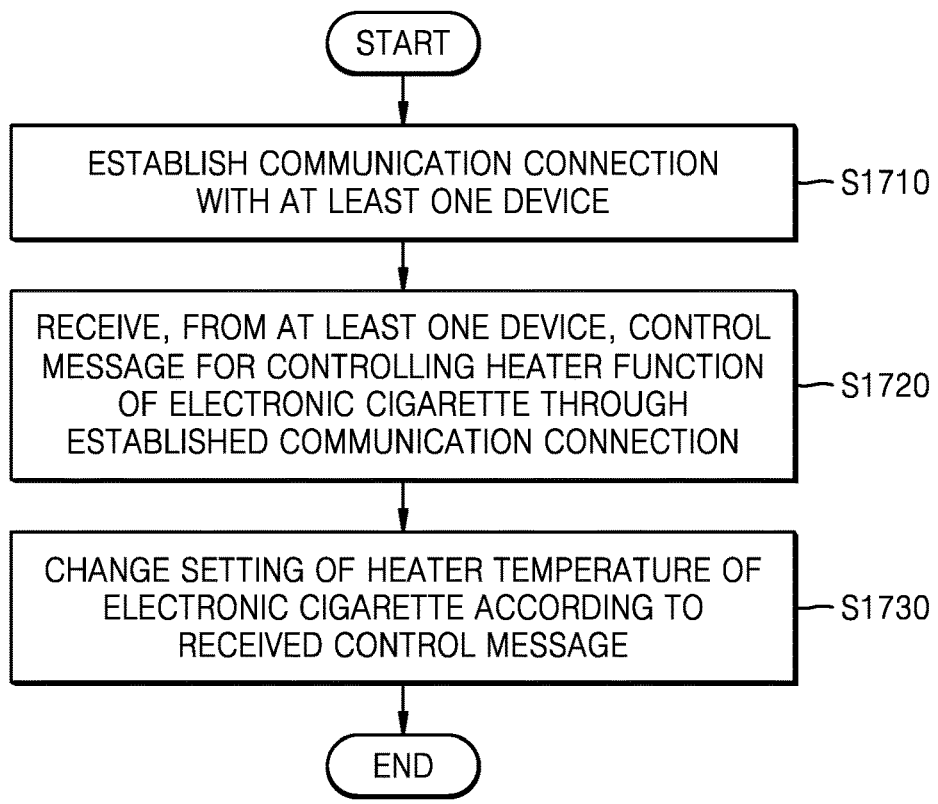
FIG. 17 is a flowchart of an example in which an electronic cigarette control device controls a heater function of an electronic cigarette by using a communication connection between a device and the electronic cigarette.

FIG. 17 is a flowchart of an example in which an electronic cigarette control device 1000 controls a heater function of an electronic cigarette 100 by using a communication connection between a device 2000 and the electronic cigarette 100.

In operation S1710, the electronic cigarette control device 1000 establishes a communication connection with at least one device 2000. This operation corresponds to S210 described above, and thus, detailed description thereof will be omitted to simplify the overall description.

In operation S1720, the electronic cigarette control device 1000 receives a control message for controlling a heater function of the electronic cigarette 100 from the at least one device 2000 through the communication connection established in operation S1710.

The heater function may include functions related to a heater. For example, the heater function may include, without limitation, a heater cleaning-related function (e.g., a function of starting operation of heater cleaning, a function of ending operation of heater cleaning, a function of determining or changing a cycle of heater cleaning, a function of determining or changing a temperature when performing heater cleaning, a function of determining or changing a period of maintaining temperature when performing heater cleaning, etc.), a heater temperature-related function (e.g., a function of determining or changing a heater temperature for heater preheating, a function of determining or changing a heater temperature for smoking, a function of determining or changing a heater temperature for puffing, a function of determining or changing a temperature variation of a heater per hour during heating, a function of determining or changing a trend in a change of a heater temperature, etc.) or the like.

In operation S1730, the electronic cigarette control device 1000 changes setting of a heater temperature of the electronic cigarette 100 according to the control message received in operation S1720.

When the device 2000 has received a user input of selecting one of the preset settings related to a plurality of heater temperatures, the electronic cigarette control device 1000 according to an exemplary embodiment may receive, from the device 2000, a control message corresponding to the user input and determine or change a setting of a heater temperature of the electronic cigarette control device 1000 such that the heater temperature corresponds to the preset setting selected according to the received control message.

For example, according to a control message corresponding to a user input of selecting one of a plurality of selection options for a heater temperature, the electronic cigarette control device 1000 may determine or change a heater temperature for cleaning, smoking or preheating of the electronic cigarette 100.

As another example, according to a control message corresponding to a user input of selecting one of a plurality of selection options related to a heater temperature, the electronic cigarette control device 1000 may determine a heater temperature for cleaning, smoking, and preheating. In this case, the electronic cigarette control device 1000 may set or change a plurality of setting values related to a temperature in accordance with one user input.

Figure 18:
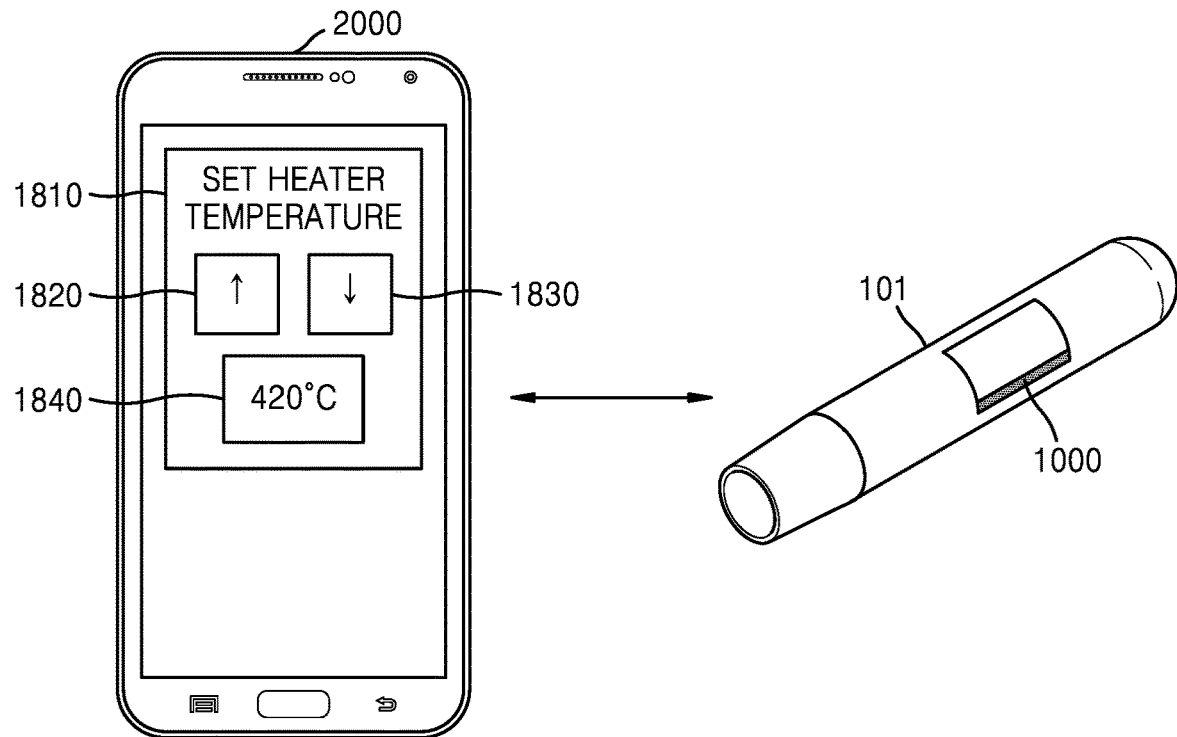
FIG. 18 is a flowchart of an example in which an electronic cigarette control device sets a heater temperature of an electronic cigarette by using a communication connection between a device and the electronic cigarette.

FIG. 18 illustrates an example in which an electronic cigarette control device 1000 sets a heater temperature of an electronic cigarette 100 by using a communication connection between a device 2000 and the electronic cigarette 100.

The electronic cigarette control device 1000 according to an exemplary embodiment may receive a control message indicating a user input applied to the device 2000 and control a holder 101 to correspond to the user input.

For example, the electronic cigarette control device 1000 may control a temperature of a heater included in the holder 101 to correspond to a target temperature determined according to a touch input on an up button 1820 and a down button 1830 displayed on a first window 1810 of the device 2000. The target temperature determined according to a touch input with respect to the up button 1820 and the down button 1830 may be displayed on a second window 1840. The target temperature may be a heater temperature for cleaning, smoking or preheating, but is not limited thereto.

Figure 19:
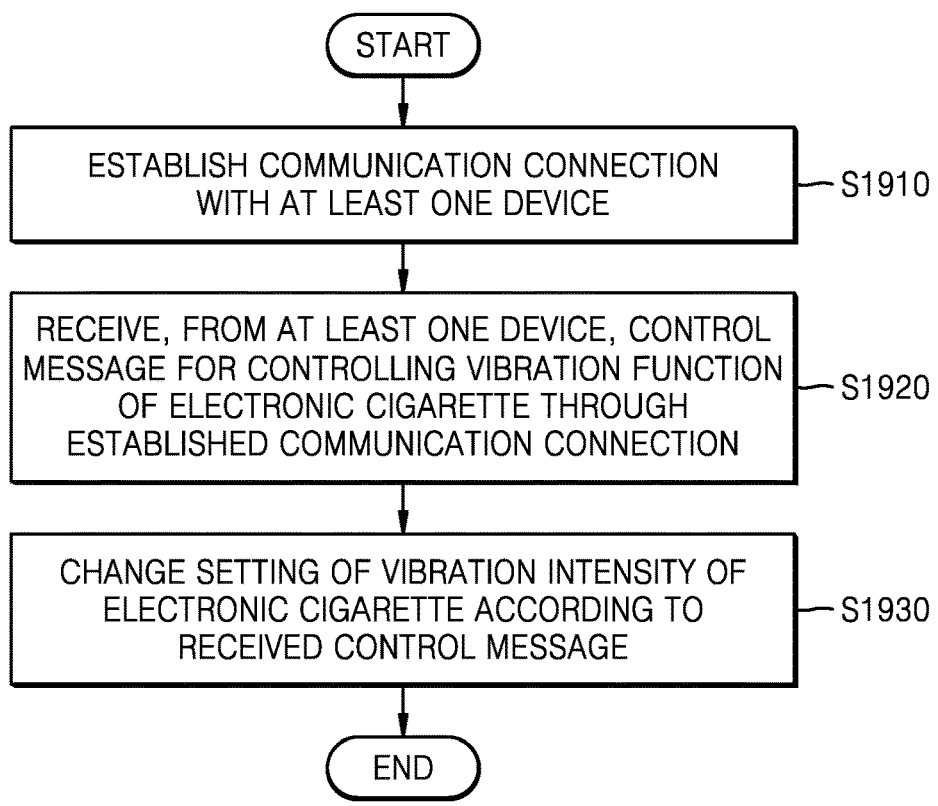
FIG. 19 is a flowchart of an example in which an electronic cigarette control device controls a vibration function of an electronic cigarette by using a communication connection between a device and the electronic cigarette.

FIG. 19 is a flowchart of an example in which an electronic cigarette control device 1000 controls a vibration function of an electronic cigarette 100 by using a communication connection between a device 2000 and the electronic cigarette 100.

In operation S1910, the electronic cigarette control device 1000 establishes a communication connection with at least one device 2000. This operation corresponds to S210 described above, and thus, detailed description thereof will be omitted to simplify the overall description.

In operation S1920, the electronic cigarette control device 1000 receives a control message for controlling a vibration function of the electronic cigarette 100 from the at least one device 2000 through the communication connection established in operation S1910.

The vibration function may include functions related to vibration. For example, the vibration function may include, without limitation, a vibration performance-related function (e.g., a vibration start function, a vibration end function, etc.), a vibration intensity-related function (e.g., a function of determining or changing a vibration intensity, a function of determining or changing a vibration intensity according to situations, a function of determining or changing a maximum vibration intensity, etc.), a vibration method-related function (e.g., a function of determining or changing a period of maintaining vibration according to situations, a function of determining or changing a current vibration method, etc.), a vibration type-related function (e.g., a function of determining or changing a type of vibration according to situations, a function of determining or changing a current vibration type), and a vibration time-related function (e.g., a function of determining whether to produce vibration according to situations, a function of determining a vibration time according to situations, etc.).

A vibration method according to an exemplary embodiment may indicate a trend in change of a vibration intensity with time. For example, a trend of a vibration produced at a vibration intensity of 70% for 1 second and then at a vibration intensity of 50% for 2 seconds may be determined as a first vibration method.

Types of vibration according to an exemplary embodiment may represent the characteristics of vibration. For example, a vibration type according to rotation of a first vibration motor and a vibration type according to rotation of a second vibration motor may be different. As another example, a vibration type when a vibration weight rotates with a first trajectory and a vibration type when the vibration weight rotates with a second trajectory may be different.

In operation S1930, the electronic cigarette control device 1000 changes a setting of a vibration intensity of the electronic cigarette 100 according to the control message received in operation S1920. While setting of a vibration intensity is described in the present operation, it will be readily understood by one of ordinary skill in the art that the present operation may be applied not only to vibration intensity but also to setting of a vibration method, a vibration type, a vibration time, or the like.

When the device 2000 has received a user input of selecting a vibration intensity, the electronic cigarette control device 1000 according to an exemplary embodiment may receive a control message corresponding to the user input, and may determine or change a setting of a vibration intensity of the electronic cigarette 100 such that the vibration intensity corresponds to a vibration intensity selected according to the received control message.

For example, according to a control message corresponding to a user input of selecting one of a plurality of vibration intensity options, the electronic cigarette control device 1000 may determine or change a vibration intensity for each situation of the electronic cigarette 100.

As another example, according to a control message corresponding to a user input of determining an intensity of a vibration motor included in the holder 101, the electronic cigarette control device 1000 may determine or change a vibration intensity for each situation of the electronic cigarette 100.

Figure 20:
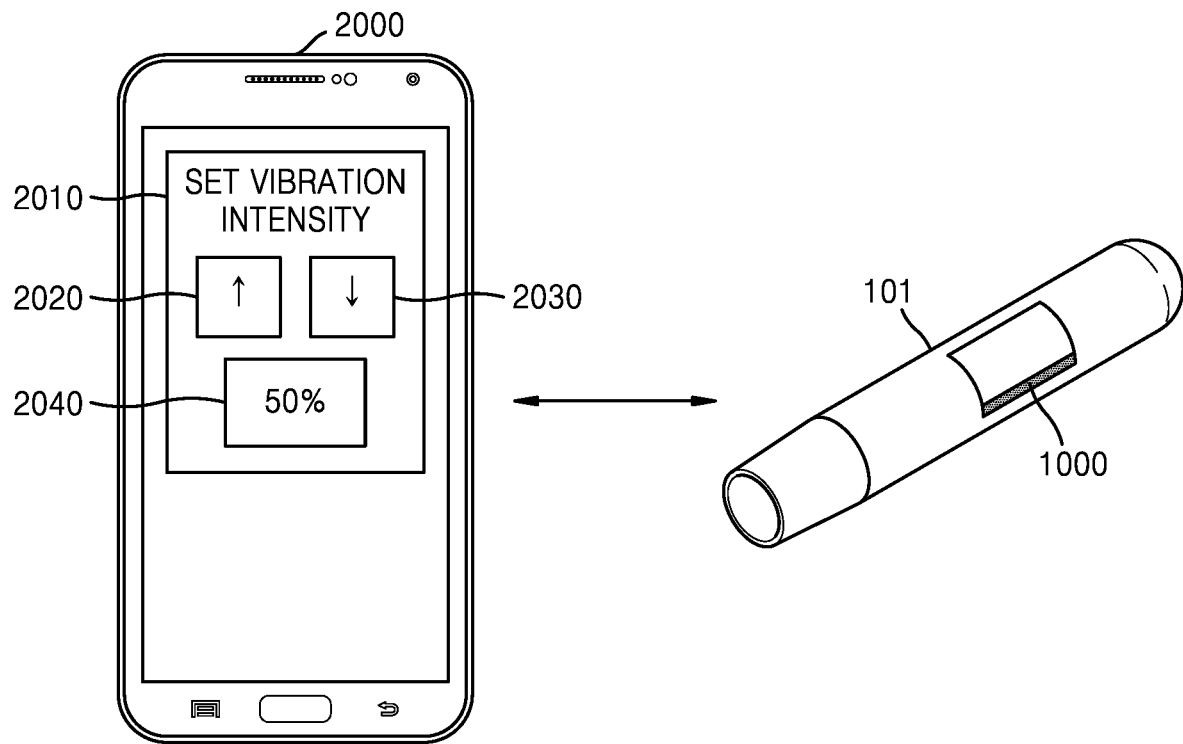
FIG. 20 illustrates an example in which an electronic cigarette control device sets a vibration intensity of an electronic cigarette by using a communication connection between a device and the electronic cigarette.

FIG. 20 illustrates an example in which an electronic cigarette control device 1000 sets a vibration intensity of an electronic cigarette 100 by using a communication connection between a device 2000 and the electronic cigarette 100.

The electronic cigarette control device 1000 according to an exemplary embodiment may receive a control message indicating a user input applied to the device 2000 and control the holder 101 to correspond to the user input.

For example, the electronic cigarette control device 1000 may control a vibration motor included in the holder 101 to correspond to a target vibration intensity determined according to a touch input on an up button 2020 and a down button 2030 displayed on a first window 2010 of the device 2000. The target vibration intensity determined according to the touch input on the up button 2020 and the down button 2030 may be numerically displayed on a second window 2040. A target vibration intensity may vary according to types of event.

Figure 21:
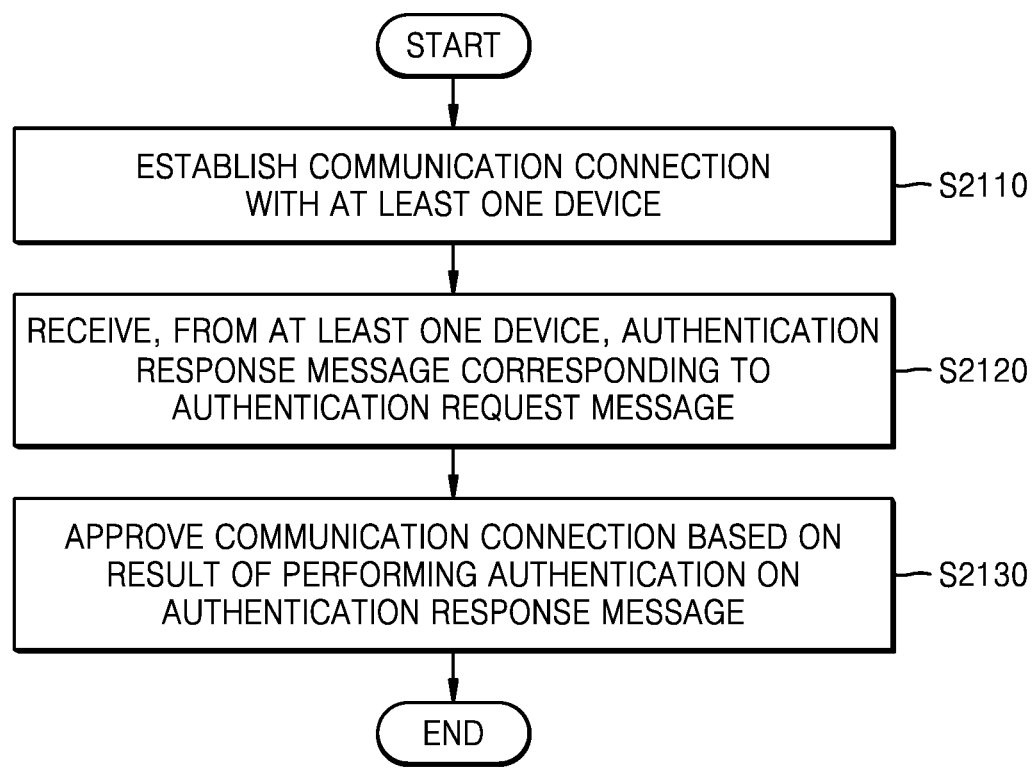
FIG. 21 is a flowchart of an example in which authentication is performed when an electronic cigarette control device establishes a communication connection between a device and an electronic cigarette.

FIG. 21 is a flowchart of an example in which authentication is performed when an electronic cigarette control device 1000 establishes a communication connection between a device 2000 and an electronic cigarette 100.

Before establishing a communication connection with the device 2000, the electronic cigarette control device 1000 may determine whether the device 2000 is approved for a communication connection. In addition, according to a result of determining whether the device 2000 is approved for a communication connection, the electronic cigarette control device 1000 may establish or deny a communication connection with the device 2000. For example, the electronic cigarette control device 1000 may only permit pairing with a device that is permitted for a communication connection with a device via Bluetooth.

In operation S2110, the electronic cigarette control device 1000 according to an exemplary embodiment transmits an authentication request message to at least one device 2000.

Upon receiving a request for a communication connection from the device 2000, the electronic cigarette control device 1000 according to an exemplary embodiment may transmit an authentication request message to the device 2000. Before completing authentication or establishing a communication connection, the electronic cigarette control device

1000 may exchange information with the device 2000 within a range of information needed for authentication.

In operation S2120, the electronic cigarette control device 1000 according to an exemplary embodiment receives, from at least one device 2000, an authentication response message corresponding to the authentication request message transmitted in S2110.

The electronic cigarette control device 1000 according to an exemplary embodiment may transmit the authentication response message to the electronic cigarette control device 1000 in accordance with the authentication request message transmitted in operation S2110.

The authentication response message may include authentication information requested in the authentication request message. For example, the authentication response message may include code information, password information, user information (for example, user's biometric information), as requested in the authentication request message.

The authentication request message and the authentication response message according to an exemplary embodiment may be encoded before being transmitted. When authentication information included in the authentication response message is encoded, information stored in the electronic cigarette control device 1000 may be required to decode the authentication information.

In operation S2130, the electronic cigarette control device 1000 according to an exemplary embodiment approves or rejects communication connection based on a result of performing authentication on the authentication response message received in operation S2130.

The electronic cigarette control device 1000 according to an exemplary embodiment may perform authentication on the authentication response message received in S2130. For example, the electronic cigarette control device 1000 may decode authentication information included in the authentication response message, and determine whether to approve communication connection by comparing the decoded authentication information with previously stored authentication information. As another example, the electronic cigarette control device 1000 may determine whether to approve communication connection based on whether the authentication response message received in operation S2130 matches authentication information that is received in real time or previously stored.

When establishing an initial communication connection, the electronic cigarette control device 1000 according to an exemplary embodiment may establish a communication connection without performing authentication. Authentication information determined in the initially established communication connection may be used in a subsequent authentication process. For example, an initial communication connection after a purchase of a product may be established without authentication, and for a second communication connection, authentication may be performed according to authentication information (for example, password information, user fingerprint information) determined in the initial communication connection.

The electronic cigarette control device 1000 according to an exemplary embodiment may establish a communication connection according to preset authentication information when establishing an initial communication connection. When authentication information has changed in the established communication connection, the changed authentication information may be used in a subsequent authentication process. For example, an initial communication connection after a purchase of a product may be established according to information included in a product manual (for example, serial number), and in a second communication connection, authentication may be performed according to authentication information determined in the initial communication connection (for example, password information, user fingerprint information).

Figure 22:
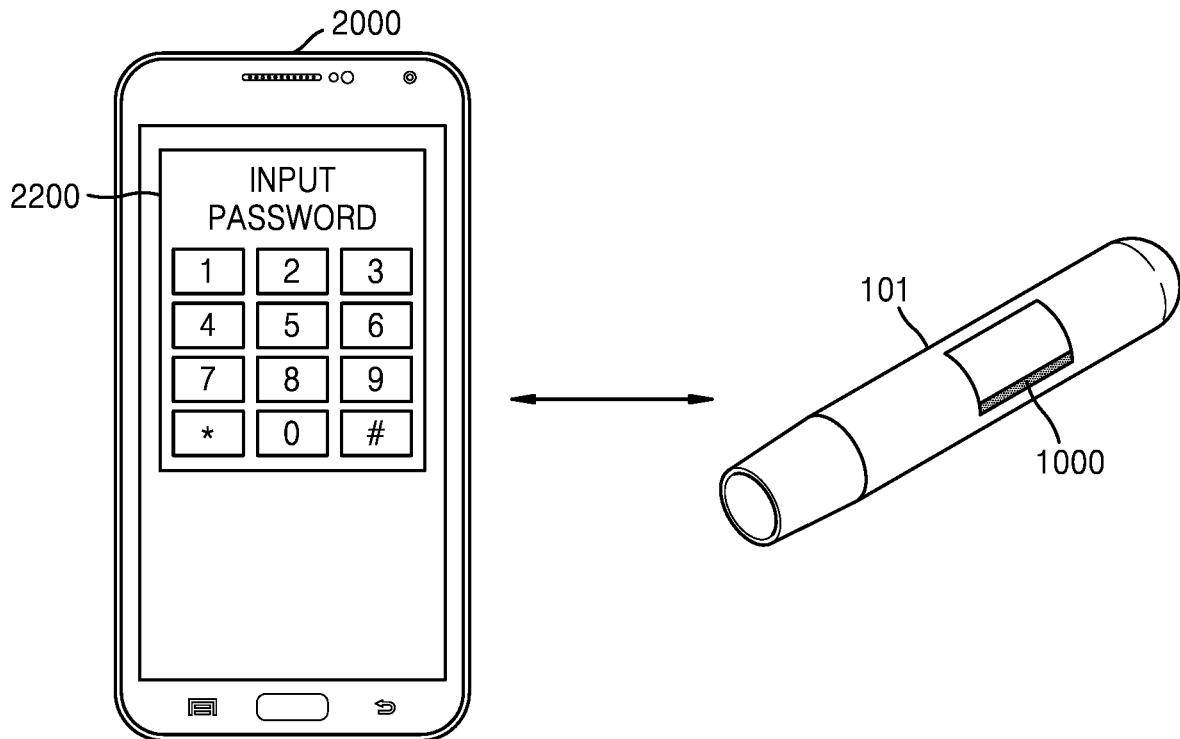
FIG. 22 illustrates an example in which authentication is performed by receiving input of a password when an electronic cigarette control device establishes a communication connection between a device and a holder.

FIG. 22 illustrates an example in which authentication is performed by receiving input of a password when an electronic cigarette control device 1000 establishes a communication connection with a holder 101.

In a process in which the device 2000 and the holder 101 establish a communication connection, a password may be used.

The electronic cigarette control device 1000 according to an exemplary embodiment may receive an authentication response message determined according to a user input on a first window 2200, and approve or deny a communication connection with the device 2000 according to a result of performing authentication with respect to the received authentication response message. For example, the electronic cigarette control device 1000 may approve a communication connection with the device 2000 when a preset password is input. When no preset password is input, the electronic cigarette control device 1000 may deny communication connection with the device 2000. When communication connection is approved, the electronic cigarette control device 1000 may establish a communication connection with the device 2000.

Figure 23:
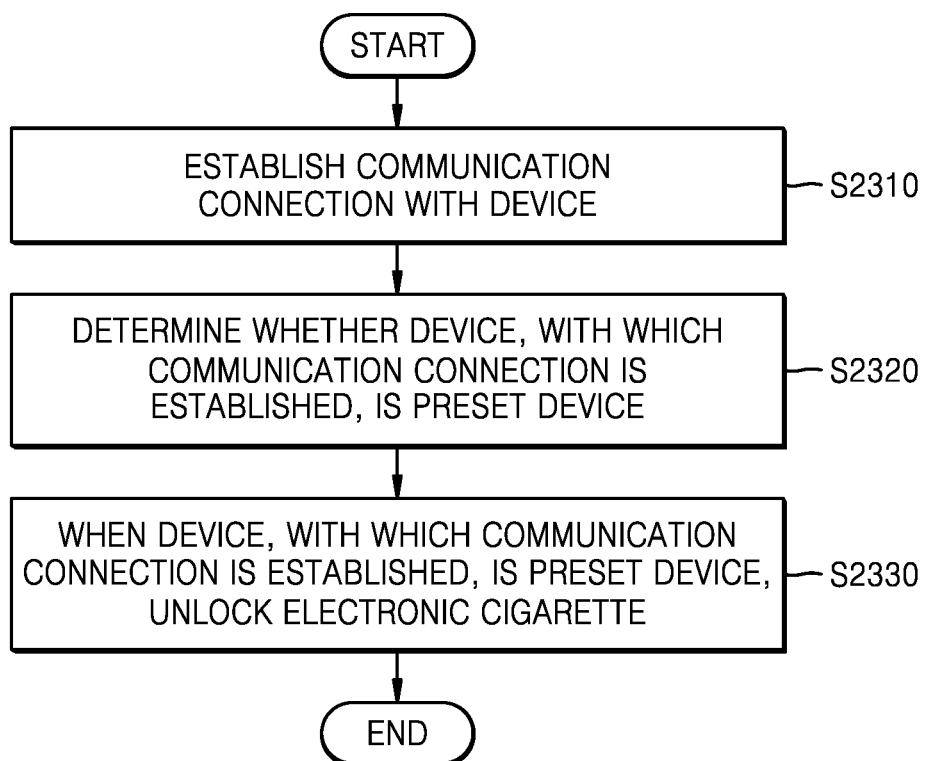
FIG. 23 is a flowchart of an example in which an electronic cigarette control device 1000 unlocks the electronic cigarette when a communication connection with a preset device is established.

FIG. 23 is a flowchart of an example in which an electronic cigarette control device 1000 unlocks the electronic cigarette when a communication connection with a preset device 2000 is established.

In operation S2310, the electronic cigarette control device 1000 establishes a communication connection with at least one device. The at least one device may be a preset device 2000 or another device (not shown) different from the preset device 2000.

The electronic cigarette control device 1000 according to an exemplary embodiment may establish a communication connection with at least one device according to a preset method. For example, when an intensity of a signal received from at least one device is equal to or higher than a preset level, the electronic cigarette control device 1000 may establish a communication connection with the at least one device. As another example, when a distance between the electronic cigarette control device 1000 and at least one device is equal to or less than a preset distance, the electronic cigarette control device 1000 may establish a communication connection with the at least one device.

In operation S2320, the electronic cigarette control device 1000 determines whether the device, with which the communication connection is established in operation S2310, is the preset device 2000 or another device (not shown).

The electronic cigarette control device 1000 may determine whether the device, with which the communication connection is established in operation S2310, is the preset device 2000 or another device (not shown), by using authentication information or the like received from the device.

A preset device may include a device, on which authentication has been performed previously. For example, a device, on which authentication is previously performed according to an authentication process and which has a history of controlling the electronic cigarette 100 by applying a user input to the electronic cigarette control device 1000, may be a preset device.

In operation S2330, when the device, with which the communication connection is established in operation S2310, is the preset device 2000, the electronic cigarette control device 1000 unlocks the electronic cigarette 100.

When the device, with which the communication connection is established in operation S2310, is the preset device 2000, the electronic cigarette control device 1000 according to an exemplary embodiment may unlock the electronic cigarette 100 and control the electronic cigarette 100 to perform an operation according to a user input.

However, when the device, with which the communication connection is established in operation S2310, is not the preset device 2000, but is another device, the electronic cigarette control device 1000 according to an exemplary embodiment may maintain the locked state of the electronic cigarette 100. When the locked state of the electronic cigarette 100 is maintained, the electronic cigarette control device 1000 may control limited operations of the electronic cigarette 100 (e.g., power on, power off, etc.) and other operations (e.g., puffing, preheating, etc.) may be restricted.

Figure 24:
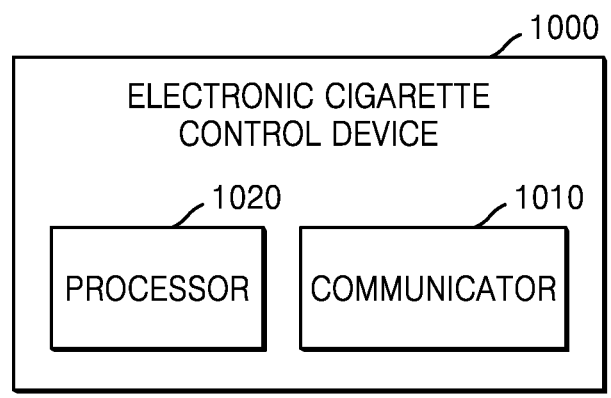
FIG. 24 is a block diagram of an example of an electronic cigarette control device.

FIG. 24 is a block diagram of an example of an electronic cigarette control device 1000.

As illustrated in FIG. 24, the electronic cigarette control device 1000 according to an exemplary embodiment may include a communicator 1010 and a processor 1020. However, the components illustrated in FIG. 24 may not be essential to the electronic cigarette control device 1000.

The electronic cigarette control device 1000 may be implemented using more components than those illustrated in FIG. 24 or the electronic cigarette control device 1000 may be implemented using fewer components than those illustrated in FIG. 24.

For example, the electronic cigarette control device 1000 according to an exemplary embodiment may further include a memory (not shown) in addition to the communicator 1010 and the processor 1020.

The communicator 1010 may perform communication with various types of external devices according to various types of communication method. The communicator 1010 may include a Wi-Fi chip, a Bluetooth chip, a wireless communication chip, an NFC chip, or the like. The processor 1020 may perform communication with various external devices by using the communicator 1010.

A Wi-Fi chip and a Bluetooth chip may perform communication using a Wi-Fi method and a Bluetooth method, respectively. When using a Wi-Fi chip or a Bluetooth chip, various types of connection information such as SSID and session keys may be first transmitted or received to establish a communication connection by using the same, and then various information may be transmitted or received. A wireless communication chip refers to a chip used to perform communication according to various communication standards such as IEEE, Zigbee, 3rd Generation (3G), 3rd Generation Partnership Project (3GPP), Long Term Evolution (LTE), or the like. An NFC chip refers to a chip operating using NFC (Near field communication) method in which a 13.56 MHz-band is used, from among various RF-ID frequency bands such as 135 kHz, 13.56 MHz, 433 MHz, 860 MHz to 960 MHz, or 2.45 GHz.

The communicator 1010 may establish a communication connection with at least one device 2000. For example, the communicator 1010 may establish a communication connection with the device 2000 by using a short-range wireless communication such as Bluetooth, etc., a local area network, a wide area, but is not limited thereto.

The processor 1020 may perform authentication during a process of establishing a communication connection with the device 2000. The processor 1020 may establish communication with the device 2000, for which authentication is successful, and deny communication with a device (not shown), for which authentication fails. Authentication performed during a process of establishing a communication connection is described above with reference to FIGS. 21 and 22.

The processor 1020 may receive a control message with respect to the electronic cigarette 100 from the at least one device 2000 through the communication connection established by the communicator 1010.

The received control message may be a message used in controlling the electronic cigarette 100. For example, the received control message may be used in controlling a communication function, a cleaning function, a storage function, a sensing function, an information reading function, a preheating function, a heater function, a vibration function, an authentication function, or the like, of the electronic cigarette 100, but is not limited thereto.

The processor 1020 according to an exemplary embodiment may receive a control message according to a user input with respect to the device 2000. For example, the processor 1020 may receive, from the communicator 1010, a control message for controlling a first function of the electronic cigarette 100 according to a user's touch input obtained during execution of an application executed on the device 2000.

The processor 1020 according to an exemplary embodiment may receive a control message according to a sensor input with respect to the device 2000. For example, the processor 1020 may receive a control message for controlling a second function of the electronic cigarette 100 according to sensing information sensed by the device 2000, such as images, motions, or positions. For example, when the device 2000 senses a two-dimensional image code, a control message corresponding to the sensed two-dimensional image code may be transmitted from the device 2000 to the communicator 1010 and from the communicator 1010 to the processor 1020. In this case, the processor 1020 may receive a control message corresponding to the sensed two-dimensional image code.

The processor 1020 according to an exemplary embodiment may receive a control message according to a user input with respect to the electronic cigarette 100. For example, a determined control message may be received according to an input applied via an input device included in the electronic cigarette 100 (for example, a button). For example, the processor 1020 may perform pairing with the device 2000 using a button included in the electronic cigarette 100.

The processor 1020 according to an exemplary embodiment may control an electronic cigarette according to the received control message. For example, according to the control message received by the communicator 1010, a communication function, a cleaning function, a storage function, a sensing function, an information reading function, a preheating function, a heater function, a vibration function, an authentication function, or the like, of the electronic cigarette 100 may be controlled. For example, according to a user's touch input obtained during execution of an application executed on the device 2000, a cleaning function, a storage function, a sensing function, an information reading function, a preheating function, a heater function, a vibration function, or the like of the electronic cigarette 100 may be executed or setting of various functions may be modified.

The method described above may be written as computer programs executable on a computer and can be implemented in general-use digital computers that execute the programs using a computer-readable recording medium. In addition, the structure of data used in the above-described method may be recorded on a computer-readable recording medium through various means. Examples of the computer-readable recording medium include magnetic storage media (e.g., ROM, RAM, USB, floppy disks, hard disks, etc.), optical recording media (e.g., CD-ROMs, or DVDs), etc.

It will be understood by one of ordinary skill in the art that various changes in form and details may be made therein without departing from the spirit and scope of the present disclosure as defined by the appended claims. Therefore, the disclosed methods should be considered in descriptive sense and not for purposes of limitation. The scope of the present disclosure is shown in the claims rather than the above-described description, and all differences within the scope will be construed as being included in the present disclosure.

The invention claimed is:

1. An electronic cigarette control device included in a holder and a cradle of an electronic cigarette, the electronic cigarette control device comprising:
    a communicator configured to establish a communication connection with at least one device; and
    a processor configured to:
        determine whether the holder and the cradle are combined, and
        in response to a control message being received from the at least one device through the established communication connection, selectively control the holder or the cradle of the electronic cigarette based on whether the holder and the cradle are combined according to the control message.

2. The electronic cigarette control device of claim 1, wherein the control message comprises a message for controlling a cleaning function of the electronic cigarette, and
    wherein the processor is further configured to change a setting of the cleaning function according to the control message.

3. The electronic cigarette control device of claim 2, wherein the processor is further configured to change a cleaning cycle of the electronic cigarette according to the control message.

4. The electronic cigarette control device of claim 1, wherein the processor is further configured to store information about a cigarette that may be inserted into the electronic cigarette.

5. The electronic cigarette control device of claim 4, wherein the processor is further configured to sense operation of a smoking function of the electronic cigarette, and transmit the information about the cigarette to the at least one device when the operation of the smoking function of the electronic cigarette is sensed.

6. The electronic cigarette control device of claim 4, wherein the information about the cigarette is obtained from an image-type code.

7. The electronic cigarette control device of claim 4, wherein the information about the cigarette comprises information about at least one of a type, a price, a purchase time, and a place of purchase of the cigarette.

8. The electronic cigarette control device of claim 1, wherein the processor is further configured to transmit a message indicating a smoking history of the electronic cigarette, to the at least one device.

9. The electronic cigarette control device of claim 1, wherein the control message comprises a message for controlling a preheating function of the electronic cigarette, and
    wherein the processor is further configured to perform preheating of the electronic cigarette according to the control message.

10. The electronic cigarette control device of claim 9, wherein the processor is further configured to transmit a message indicating a progress status or completion of preheating of the electronic cigarette to the at least one device.

11. The electronic cigarette control device of claim 1, wherein the processor is further configured to transmit information about the electronic cigarette to the at least one device.

12. The electronic cigarette control device of claim 11, wherein the information about the electronic cigarette comprises at least one of remaining battery power information of the electronic cigarette, information about the number of times of using a holder, and information about estimated lifetime of the electronic cigarette.

13. The electronic cigarette control device of claim 1, wherein the control message comprises a message for controlling a heater function of the electronic cigarette, and
    wherein the processor is further configured to change a setting of a heater temperature of the electronic cigarette according to the control message.

14. The electronic cigarette control device of claim 1, wherein the control message comprises a message for controlling a vibration function of the electronic cigarette, and
    the processor is further configured to change a setting of a vibration intensity of the electronic cigarette according to the control message.

15. The electronic cigarette control device of claim 1, transmits an authentication request message to the at least one device,
    receives an authentication response message corresponding to the authentication request message from the at least one device, and
    approves the communication connection according to a result of authentication regarding the authentication response message.

16. The electronic cigarette control device of claim 1, wherein the processor is further configured to
    determine whether the at least one device, with which the communication connection is established, is a preset device,
    unlock the electronic cigarette based upon a determination that the at least one device is the preset device, and
    control the at least one device according to a user input, after the electronic cigarette is unlocked.

* * * * *